(12) United States Patent
Zur

(10) Patent No.: US 10,929,669 B2
(45) Date of Patent: Feb. 23, 2021

(54) SYSTEMS AND METHODS FOR PROCESSING COLON IMAGES AND VIDEOS

(71) Applicant: Magentiq Eye LTD, Haifa (IL)

(72) Inventor: Dror Zur, Haifa (IL)

(73) Assignee: Magentiq Eye LTD, Haifa (IL)

(*) Notice: Subject to any disclaimer, the term of this patent is extended or adjusted under 35 U.S.C. 154(b) by 16 days.

(21) Appl. No.: 16/430,461

(22) Filed: Jun. 4, 2019

(65) Prior Publication Data
US 2020/0387706 A1   Dec. 10, 2020

(51) Int. Cl.
| | |
|---|---|
| *G06T 7/73* | (2017.01) |
| *G06K 9/00* | (2006.01) |
| *G06T 15/08* | (2011.01) |
| *G06T 7/62* | (2017.01) |
| *H04N 5/262* | (2006.01) |
| *G06T 7/55* | (2017.01) |
| *G06T 7/246* | (2017.01) |
| *A61B 1/00* | (2006.01) |
| *A61B 1/31* | (2006.01) |

(Continued)

(52) U.S. Cl.
CPC ........ *G06K 9/00671* (2013.01); *A61B 1/0005* (2013.01); *A61B 1/31* (2013.01); *G06T 7/246* (2017.01); *G06T 7/55* (2017.01); *G06T 7/62* (2017.01); *G06T 7/73* (2017.01); *G06T 15/08* (2013.01); *H04N 5/23222* (2013.01); *H04N 5/2628* (2013.01); *G06K 2209/053* (2013.01); *G06T 2200/24* (2013.01); *G06T 2207/10068* (2013.01); *G06T 2207/20081* (2013.01); *G06T 2207/20084* (2013.01); *G06T 2207/30032* (2013.01); *G06T 2207/30244* (2013.01); *G16H 30/40* (2018.01); *H04N 2005/2255* (2013.01)

(58) Field of Classification Search
CPC combination set(s) only.
See application file for complete search history.

(56) References Cited

U.S. PATENT DOCUMENTS

| | | | |
|---|---|---|---|
| 8,249,687 B2 * | 8/2012 | Peterson | A61B 6/032 600/407 |
| 8,795,157 B1 * | 8/2014 | Yaron | A61B 1/31 600/111 |

(Continued)

OTHER PUBLICATIONS

International Search Report and the Written Opinion dated Aug. 12, 2020 From the International Searching Authority Re. Application No. PCT/IL2020/050497. (9 Pages).

*Primary Examiner* — Andrew G Yang

(57) ABSTRACT

There is provided a method of generating instructions for presenting a graphical user interface (GUI) for dynamically tracking at least one polyp in a plurality of endoscopic images of a colon of a patient, comprising: iterating for the plurality of endoscopic images: tracking a location of a region depicting at least one polyp within the respective endoscopic image relative to at least one previous endoscopic image, when the location of the region is external to the respective endoscopic image: computing a vector from within the respective endoscopic image to the location of the region external to the respective endoscopic image, creating an augmented endoscopic image by augmenting the respective endoscopic image with an indication of the vector, and generating instructions for presenting the augmented endoscopic image within the GUI.

10 Claims, 15 Drawing Sheets

(51) Int. Cl.
*H04N 5/232* (2006.01)
*H04N 5/225* (2006.01)
*G16H 30/40* (2018.01)

(56) References Cited

U.S. PATENT DOCUMENTS

| | | | |
|---|---|---|---|
| 2005/0251017 A1* | 11/2005 | Azar | A61B 5/06 600/407 |
| 2008/0058593 A1* | 3/2008 | Gu | G06T 5/006 600/109 |
| 2009/0023993 A1* | 1/2009 | Davidson | A61B 1/041 600/109 |
| 2009/0268865 A1* | 10/2009 | Ren | A61B 6/544 378/37 |
| 2016/0171158 A1* | 6/2016 | Park | G06F 3/04847 715/771 |
| 2017/0258295 A1* | 9/2017 | Kronman | A61B 1/018 |
| 2018/0253839 A1 | 9/2018 | Zur | |
| 2018/0296281 A1 | 10/2018 | Yeung et al. | |
| 2019/0080454 A1* | 3/2019 | Hameed | A61B 1/0014 |
| 2019/0138786 A1* | 5/2019 | Trenholm | G06T 7/50 |
| 2019/0268538 A1* | 8/2019 | Shiratani | A61B 1/06 |
| 2019/0297276 A1* | 9/2019 | Sachdev | A61B 1/00009 |
| 2019/0385302 A1* | 12/2019 | Ngo Dinh | A61B 1/00009 |
| 2020/0219272 A1* | 7/2020 | Pizer | G06K 9/00744 |

\* cited by examiner $$T = \begin{matrix} 1.0156 & 0.0006 & -15.4773 \\ -0.0006 & 1.0156 & 5.4384 \\ 0 & 0 & 1.0000 \end{matrix}$$

502

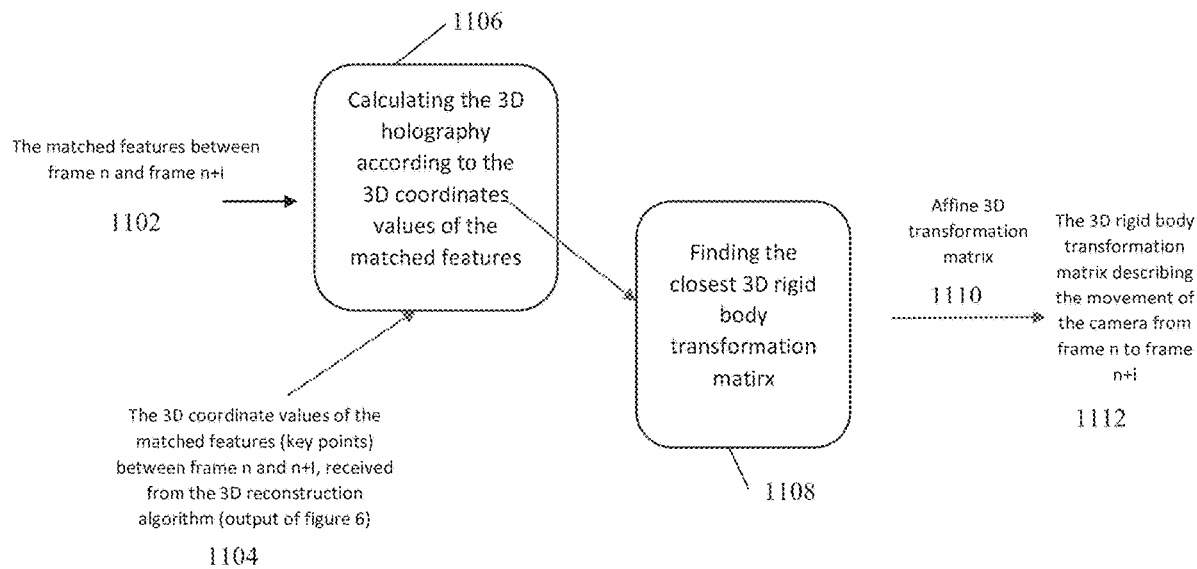

FIG. 9

$$\begin{pmatrix} \cos\alpha\cos\beta & \cos\alpha\sin\beta\sin\gamma - \sin\alpha\cos\gamma & \cos\alpha\sin\beta\cos\gamma + \sin\alpha\sin\gamma & x_t \\ \sin\alpha\cos\beta & \sin\alpha\sin\beta\sin\gamma + \cos\alpha\cos\gamma & \sin\alpha\sin\beta\cos\gamma - \cos\alpha\sin\gamma & y_t \\ -\sin\beta & \cos\beta\sin\gamma & \cos\beta\cos\gamma & z_t \\ 0 & 0 & 0 & 1 \end{pmatrix}$$

Roll by $\gamma$, Pitch by $\beta$, Yaw by $\alpha$, Translate by $(x_t, y_t, z_t)$

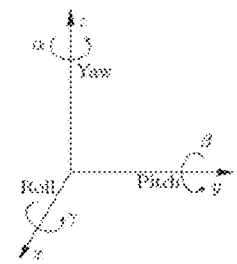

SYSTEMS AND METHODS FOR PROCESSING COLON IMAGES AND VIDEOS

FIELD AND BACKGROUND OF THE INVENTION

The present invention, in some embodiments thereof, relates to colonoscopy and, more specifically, but not exclusively, to systems and methods for processing colon images and video, and/or processing colon polyps automatically detected during a colonoscopy procedure.

Colonoscopy is the gold standard for detection of colonic polyps. During colonoscopy, a long flexible tube called a colonoscope is advanced within the colon. A video camera at the end of the colonoscope captures images, which are presented on a display to the physician. The physician examines the internal surface of the colon for the presence of polyps. Identified polyps are removed using instruments of the colonoscope. Early removal of cancerous polyps may eliminate or reduce risk of colon cancer.

SUMMARY OF THE INVENTION

According to a first aspect, a method of generating instructions for presenting a graphical user interface (GUI) for dynamically tracking at least one polyp in a plurality of endoscopic images of a colon of a patient, comprises: iterating for the plurality of endoscopic images: tracking a location of a region depicting at least one polyp within the respective endoscopic image relative to at least one previous endoscopic image, when the location of the region is external to the respective endoscopic image: computing a vector from within the respective endoscopic image to the location of the region external to the respective endoscopic image, creating an augmented endoscopic image by augmenting the respective endoscopic image with an indication of the vector, and generating instructions for presenting the augmented endoscopic image within the GUI.

According to a second aspect, a method of generating instructions for presenting a GUI for dynamically tracking 3D movement of an endoscopic camera capturing a plurality of 2D endoscopic images within a colon of a patient, comprises:

iterating for respective endoscopic images of a plurality of endoscopic images: feeding the respective 2D endoscopic image into a 3D reconstruction neural network, outputting by the 3D reconstruction neural network, a 3D reconstruction of the respective 2D endoscopic image, wherein pixels of the 2D endoscopic image are assigned 3D coordinates, computing according to the 3D reconstruction, a current 3D location within the colon of the endoscopic camera, and generating instructions for presenting the current 3D location of the endoscopic camera on a colon map within the GUI.

According to a third aspect, a method of computing a three dimensional volume of a polyp based on at least one two dimensional (2D) image, comprises: receiving at least one 2D image of an internal surface of a colon captured by an endoscopic camera located within a lumen of the colon, receiving an indication of a region of the at least one 2D image depicting at least one polyp, feeding the at least one 2D image into a 3D reconstruction neural network, outputting by the 3D reconstruction neural network, a 3D reconstruction of the at least one 2D image, wherein pixels of the 2D image are assigned 3D coordinates, and computing an estimated 3D volume of the at least one polyp within the region of the at least one 2D image according to an analysis of the 3D coordinates of pixels of the region of the at least one 2D image.

In a further implementation of the first aspect, the indication of the vector depicts a direction and/or orientation for adjustment of an endoscopic camera for capturing another at least one endoscopic image depicting the region of the at least one image.

In a further implementation of the first aspect, when the location of the region depicting at least one polyp appears in the respective endoscopic image, the augmented image is created by augmenting the respective endoscopic image with the location of the region, wherein the indication of the vector is excluded from the augmented endoscopic image.

In a further implementation of the first aspect, further comprising: computing a location of the region depicting at least one polyp within the colon of the patient, creating a colon map by marking a schematic representing the colon of the patient with an indication denoting the location of the region depicting the at least one polyp, and generating instructions for presenting within the GUI, the colon map, wherein the colon map is dynamically updated with locations of new detected polyps.

In a further implementation of the first aspect, further comprising: translating and/or rotating at least one endoscopic image of a sequential sub-set of the plurality of endoscopic images including the respective endoscopic image for creating a processed sequential sub-set of the plurality of endoscopic images wherein the region depicting the at least one polyp is at a same approximate position in all of the images of the sequential sub-set of the plurality of endoscopic image, feeding, into a detection neural network, the processed sequential sub-set of the plurality of endoscopic images, outputting by the detection neural network, a current region depicting the at least one polyp for the respective endoscopic image, creating an augmented image of the respective endoscopic image by augmenting the respective endoscopic image with the current region, and generating instructions for presenting the augmented image within the GUI.

In a further implementation of the first aspect, when the output of the neural network is provided for a previous endoscopic image that is sequentially earlier than the respective endoscopic image and the tracked location of the region depicting at least one polyp within the respective endoscopic image is at a different location than the region outputted by the neural network for the previous endoscopic image, creating the augmented image for the respective endoscopic image based on the tracked location.

In a further implementation of the second aspect, further comprising: tracking 3D locations of the endoscopic camera, and plotting the tracked 3D locations of the endoscopic camera within the colon map GUI.

In a further implementation of the second aspect, forward direction tracked 3D locations of the endoscopic camera are marked on the colon map presented in the GUI with a marking denoting a forward direction of the endoscopic camera entering deeper into the colon, and reverse direction tracked 3D locations of the endoscopic camera presented on the colon map are marked with another marking denoting a reverse direction of the endoscopic camera being removed from the colon.

In a further implementation of the second aspect, further comprising: feeding the respective endoscopic image into a detection neural network, outputting, by the detection neural network, an indication of a region of the endoscopic image depicting at least one polyp, and computing an estimated 3D location of the at least one polyp within the region of the endoscopic image according to the 3D reconstruction, and generating instructions for presenting the 3D location of the at least one polyp on a colon map within the GUI.

In a further implementation of the second aspect, further comprising: receiving an indication of surgical removal of the at least one polyp from the colon, and marking the 3D location of the at least one polyp on the colon map with an indication of removal of the at least one polyp.

In a further implementation of the second aspect, further comprising: tracking a 3D location of an endoscopic camera capturing the plurality of endoscopic images, computing an estimating distance from a current 3D location of the endoscopic camera to a 3D location of at least one polyp previously identified using earlier obtained endoscopic images, and generating instructions for presenting an indication within the GUI when the estimated distance is below a threshold.

In a further implementation of the second aspect, further comprising: analyzing the respective 3D reconstruction to estimate a portion of an inner surface of the colon depicted within the respective endoscopic image, tracking cumulative portions of the inner surface of the colon depicted within successive endoscopic images during a spiral scanning motion of the endoscopic camera during a colonoscopy procedure, and generating instructions for presenting within the GUI, at least one of: an estimate of remaining portions of the inner surface not yet depicted within any previously captured endoscopic images, and an estimate of total coverage of the of the inner surface area, wherein the analyzing, the tracking, and the generating are iterated during the spiral scanning motion In a further implementation of the second aspect, each portion corresponds to a time window having an interval corresponding to an amount of time for covering the respective portion during the spiral scanning motion, wherein an indication of adequate converge is generated when at least one image depicting mostly the respective portion is captured during the time window and/or another indication of inadequate coverage is generated when no images depicting mostly the respective portion are captured during the time window.

In a further implementation of the second aspect, an indication of a total amount of the inner surface depicted in images relative to an amount of non-depicted inner surface is computed by aggregating the portions covered during the spiral scanning motion relative to the portions not covered during the spiral scanning motion.

In a further implementation of the second aspect, the 3D reconstruction neural network is trained by a training dataset of pairs of 2D endoscopic images defining input images corresponding 3D coordinate values computed for pixels of the 2D endoscopic images computed by a 3D reconstruction process defining ground truth.

In a further implementation of the second aspect, further comprising: receiving an indication of at least one anatomical landmark of the colon, wherein the at least one anatomical landmark divides the colon into a plurality of parts, tracking 3D locations of the endoscopic camera relative to the at least one anatomical landmark, computing an amount of time spent by the endoscopic camera in each of the plurality of parts of the colon, and generating instructions for presenting the amount of time spent by the endoscopic camera in each of the plurality of parts of the colon in the GUI.

In a further implementation of the third aspect, the indication of the region of the at least one 2D image depicting at least one polyp is outputted by a detection neural network trained for segmenting polyps in 2D images.

In a further implementation of the third aspect, the 3D reconstruction of the at least one 2D image is fed into the detection neural network in combination with the at least one 2D image for outputting the indication of the region depicting the at least one polyp.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings:

FIG. 9 is a flowchart depicting an exemplary 3D tracking process for tracking 3D movement of the camera, in accordance with some embodiments of the present invention;

FIG. 10 is an example of a 3D rigid body transformation matrix for tracking 3D movement of a colonoscopy camera, in accordance with some embodiments of the present invention;

DETAILED DESCRIPTION OF SPECIFIC EMBODIMENTS OF THE INVENTION

Figure 1:
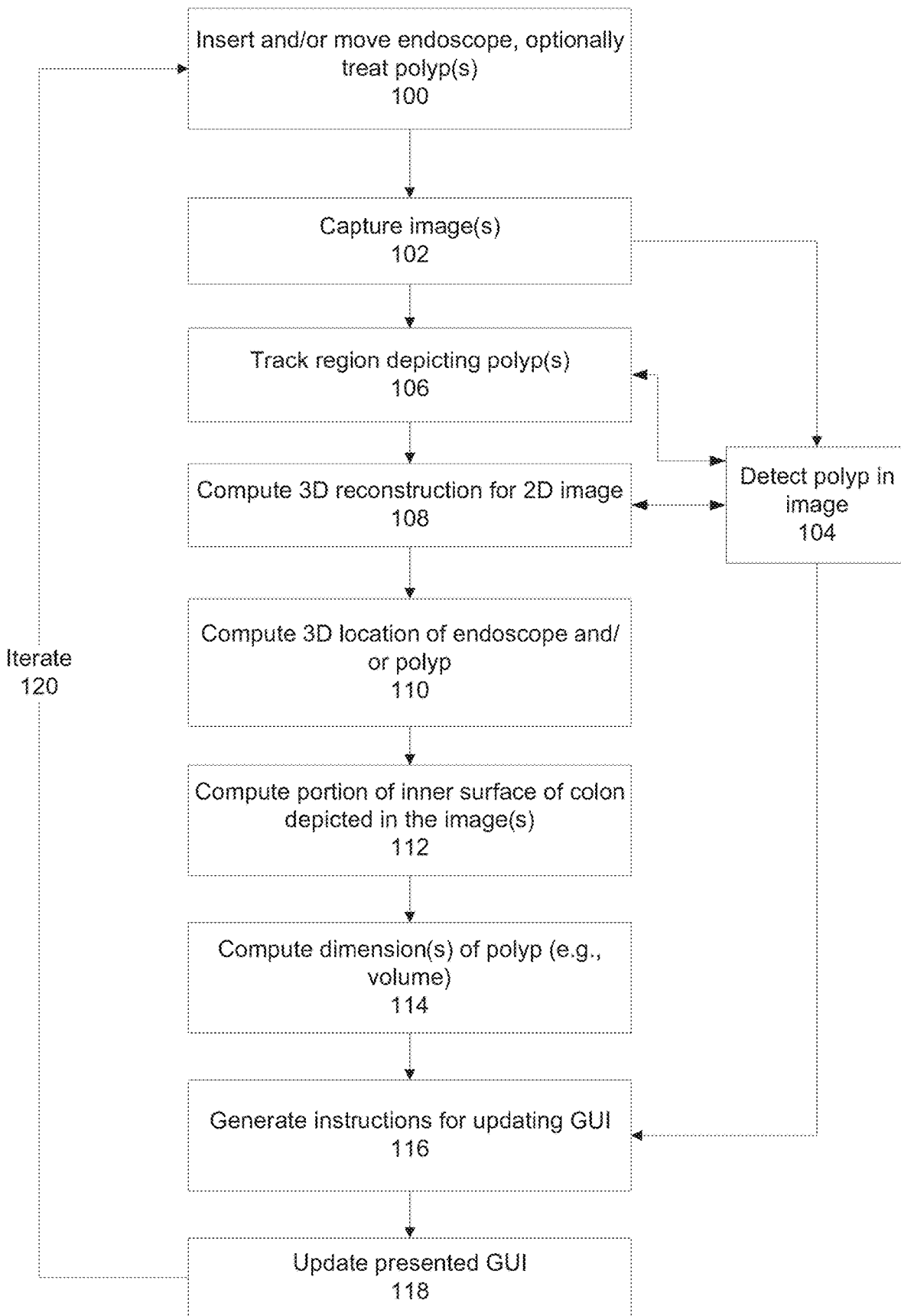
FIG. 1 is a is a flowchart of a method for processing images acquired by a camera located on an endoscope within a colon of a target patient, in accordance with some embodiments of the present invention.

The present invention, in some embodiments thereof, relates to colonoscopy and, more specifically, but not exclusively, to systems and methods for processing colon images and video, and/or processing colon polyps automatically detected during a colonoscopy procedure.

As used herein, the term image and frame are sometimes interchangeable. The images captured by a camera of the colonoscope may be individual frames of a video captured by the camera.

As used herein, the term endoscope and colonoscope are sometimes interchangeable.

An aspect of some embodiments of the present invention relates to systems, methods, an apparatus, and/or code instructions (i.e., stored on a memory and executable by one or more hardware processors) for generating instructions for presenting a graphical user interface (GUI) for dynamically tracking one or more polyps in two dimensional (2D), optionally color, endoscopic images of a colon of a patient captured by a camera of an endoscope located within a lumen of the colon, for example, during a colonoscopy procedure. The location of a region depicting one or more polyps (e.g., region of interest (ROI) within a current endoscopic image is tracked relative to one or more previous endoscopic images, optionally based on matching visual features between the current and previous images, for example, features extracted based on the speed robust features (SURF) process. When the location of the ROI depicting the polyp(s) is determined, for the current image, to be located externally to the borders of the image, a vector is computed. The vector points from a location of within the current image to the location of the ROI located externally to the current image. The location within the current image may be, for example, the location on the screen of the ROI in earlier images when the ROI was located within the image. An augmented endoscopic image is created by augmenting the current endoscopic image with the indication of the vector, for example, by injecting the indication of the vector as a GUI element into the endoscopic image, and/or as an overlay. Instructions are generated for presenting the augmented endoscopic image on a display within the GUI.

The indication of the vector depicts a direction and/or orientation for adjustment of the endoscopic camera for capturing another endoscopic image depicting the ROI of the polyp(s). The augmented endoscopic image is augmented with the indication of the vector for display within the GUI.

The indication of the vector may be an arrow, pointing towards the location of the ROI external to the image. Moving the camera in the direction of the arrow restores the polyp within the images.

The process is iterated for the captured images, assisting the operator in maintaining the polyp within the image. When the camera moves and the polyp no longer appears in the current image, the indication of the vector directs the operator as to how to maneuver the camera in order to re-capture the polyp within the images.

An aspect of some embodiments of the present invention relates to systems, methods, an apparatus, and/or code instructions (i.e., stored on a memory and executable by one or more hardware processors) for generating instructions for dynamically tracking 3D movement of an endoscopic camera capturing endoscopic images within a colon of a patient. Captured 2D images (e.g., each image, or every few images, for example, every third or fourth or other number of images) are fed into a 3D reconstruction neural network, optionally a convolutional neural network (CNN). The 3D reconstruction neural network outputs a 3D reconstruction of the respective 2D endoscopic image. Pixels of the 2D endoscopic image are assigned 3D coordinates. A current 3D location of the endoscopic camera (i.e., the endoscope) within the colon is computing according to the 3D reconstruction. For example, the 3D location of the endoscope is determined based on the values of the 3D coordinates of the current image. Instructions for presenting the current 3D location of the endoscopic camera on a colon map within the GUI are generated. The colon map depicts a virtual map of the colon of the patient.

The 3D locations of the endoscope may be tracked and plotted as a trajectory on the colon map, for example, tracing the path of the endoscope within the colon during the colonoscopy procedure.

Forward and reverse directions of the endoscope may be marked, for example, by arrows and/or color coding.

3D locations of detected polyps may be marked on the colon map. The 3D location of the detected polyp may be tracked relative to the 3D location of the camera. When the distance between the camera and the polyp is below a threshold, instructions for presenting an indication within the GUI may be generated. The indication may be, for example, a marking of the polyp when the polyp is present in the image, an arrow pointing to the location of the polyp when the polyp is not depicted in the image, and/or a message that the camera is in proximity to the polyp, optionally within instructions on how to move the camera to capture images depicting the polyp.

Polyps that were surgically removed from the colon may be marked on the colon map.

Optionally, the portion of the inner surface of the colon depicted within the images is analyzed. For example, based on a virtual division of the inner surface into quarters. Coverage of the portions is cumulatively tracked as the colonoscope is used to visually scan the inner wall of the colon, optionally continuously, for example, in a spiral motion as the colonoscope is being pulled out of the colon (or being moved forward in the colon). The spiral motion is, for example, performed by clockwise (or anti-clockwise) orientation of the camera as the colonoscope is slowly being pulled out (or pushed in). Alternatively, the inner portion of the colon is imaged in steps, for example, the colonoscope is pulled back (or pushed forward) a certain distance, the reverse (or forward) motion of the camera is stopped, and the circumference is imaged by orienting the camera in a circle pattern (or cross wise pattern), where the pulling back (or pushing forward), the stopping, and the imaging is iterated over the length of the colon. Optionally, each portion (e.g., quarter) is mostly depicted by one or more images as the colonoscope is used to visually scan the inner wall of the colon. An estimate of the depicted inner surface and/or remaining inner surface (e.g., quarters) may be generated and instructions generated for presentation within the GUI. The estimate may be performed in real time, for example, per quarter, and/or as a global estimate for the whole (or most of) the colon based on an aggregation of coverage of individual portions (e.g., quarters). The previously covered and/or remaining coverage of the inner surface of the colon helps the operator to ensure that the entire inner surface of the colon has been captured in images, reducing risk of missed polyps.

Optionally, an amount of time spent by the colonoscope in one or more defined portions of the colon is computed based on the 3D tracking of the colonoscope. Instructions for presentation of the time may be generated for presentation within the GUI, for example, the amount of time spent in each portion of the colon is presented on the corresponding portion of the colon map.

An aspect of some embodiments of the present invention relates to systems, methods, an apparatus, and/or code instructions (i.e., stored on a memory and executable by one or more hardware processors) for generating instructions for computing a dimension (e.g., size) of a polyp. The dimension may be a 2D dimension, for example, area and/or radius of a flat polyp, and/or a 3D dimension, for example, volume and/or radius of a raised polyp. An indication of a region of the 2D image depicting the polyp(s) is received, for example, manually delineated by the operator (e.g., using the GUI), and/or outputted by a detection neural network that is fed the 2D image(s) and trained for segmenting polyps in 2D images. The 2D image is fed into a 3D reconstruction neural network that outputs 3D coordinates for the pixels of the 2D image. The dimension of the polyp is computed according to an analysis of the 3D coordinates of pixels of the ROI of the 2D image depicting the polyp.

Optionally, instructions for presenting an alert within the GUI are generated when the dimension of the polyp is above a threshold. The threshold may define the minimum dimension of polyps that should be removed. Polyps having dimensions below the threshold may be left in place.

At least some implementations of the systems, methods, apparatus, and/or code instructions described herein relate to the medical problem of treating a patient, in particular, for identifying and removing polyps within a colon of a patient. Using standard colonoscopy procedures, adenomas may be missed in up to 20% of cases, and cancer may be are missed in about 0.6%, as evidenced by ultimate detection of these missed lesions at interval colonoscopy. Adenoma detection rate (ADR) is variable, and depends on the patient's risk factors, physician's performance and instrumental limitations. Patient's individual anatomy and the quality of bowel preparation are important determinants of quality colonoscopy. The performance of quality colonoscopy by the physician depends on factors such as successful cecal intubation, careful inspection during extended withdrawal time and overall endoscopic experience. Endoscopist fatigue and inattention are risk factors that can cause the physician to miss polyps whereas earlier procedure start time in a session correlates with better outcomes. Noteworthy is that the ADR increased in sites that underwent a quality improvement program, whereas awareness of monitoring or simply being observed positively influenced the ADR for the better.

At least some implementations of the systems, methods, apparatus, and/or code instructions described herein improve the detection and/or removal rate of polyps during a colonoscopy procedures. The improvement is facilitated, at least in part, by the GUI described herein, which helps direct the operator to: (i) previously identified polyps which have disappeared from the current captured image by an arrow pointing in the direction for maneuvering of the colonoscope camera to re-capture image(s) of the polyp, helping ensure that the polyp is not missed or mistaken for another polyp (ii) presenting and updating a colon map that displays 2D and/or 3D locations of identified polyps, to help make sure that all identified polyps have been evaluated and/or removed (iii) tracking portions of the inner surface circumference of the colon to identify portions of the inner surface which have not been captured by images and therefore not analyzed to identify polyps, to help make sure that no part of the colon remains un-imaged and polyps are missed, (iv) computation of volume of polyps, which may aid in determining which polyps to remove and/or provides data to assist in diagnosis of cancer, and/or (v) computing an amount of time spent by the colonoscope in each part of the colon. The GUI may be presented and adapted in real time for images captured during the colonoscopy procedure, for real time feedback in helping guide the physician operator to improve the polyp detection and/or removal rate.

At least some implementations of the systems, methods, apparatus, and/or code instructions described herein address the technical problem of devices that improve the polyps detection and/or removal rate. In particular, at least some implementations of the systems, methods, apparatus, and/or code instructions described herein improve the technology of image processing and/or the technology of GUI, by code that analyzes the captured images, and/or the GUI that is used by the operator to help increase the polyp identification and/or detection rate. For example, in comparison to standard approaches. For example, optics that achieve a wider field of view and improve picture resolution, and distal colonoscope attachments such as balloons caps or rings to improve visualization behind mucosal folds. Such optical and attachment devices are passive and rely on the skill of the operator in tracking the identified polyps. In contrast, the GUI described herein automatically tracks the identified polyps.

At least some implementations of the systems, methods, apparatus, and/or code instructions described herein address the technical problem of computing a volume of a polyp. Based on standard practices, the size of the polyp is only measured after the polyp has been removed from the patient, for example, as described with reference to Kuine, Keiichiro, et al. *"Endoscopic measurement of polyp size using a novel calibrated hood." Gastroenterology research and practice* 2014 (2014). The importance of measuring the polyp size is described, for example, with reference to Summers, Ronald M. *"Polyp size measurement at CT colonography: What do we know and what do we need to know?." Radiology* 255.3 (2010): 707-720. In contrast, at least some of the systems, methods, apparatus, and/or code instructions described herein compute the size of the polyp in-vivo, while the polyp is attached to the colon wall, before the polyp has been removed. Computing the volume of the polyp before it's removed may provide some advantages, for example, polyps above a threshold volume may be targeted for removal and/or polyps below the threshold volume may be left in the body of the patient. The volume of the polyp computed prior to removal may be compared to the volume after removal, for example, to determine whether the entire polyp has been removed, and/or to compare the volume of polyp above the surface to the unseen part of the polyp below the surface as a risk for cancer, and/or to help grade the polyp and/or risk of cancer.

At least some implementations of the systems, methods, apparatus, and/or code instructions described herein address the technical problem of neural network processing that is slower than the rate of images captured in a video by a camera of a colonoscope. The process described herein for tracking polyps (and/or associated ROIs) based on extracted features compensates for delays in a process for detecting polyps using a neural network that outputs data for the images, optionally an indication of a detected polyp and/or location thereof. The neural network based detection process is more computationally expensive than the feature extraction and tracking process (e.g., 25 milliseconds (ms)-40 ms on typical personal computer (PC) with 17 Intel processor and Nvidia GTK 1080 TI GPU while the typical time difference between successive frames is in the range of 20 ms-40 ms). As such, a delay scenario may be created in the sense that the detection results outputted by the neural network for frame number denoted i are ready only when a subsequent frame (e.g., number denoted i+2, or later frame) is already presented. Such delay scenario may result in a bizarre situation when the initial frame depicts the polyp but the later frame does not depict the polyp (e.g., camera shifted position so that the polyp is not captured in the image), and the delay in the neural network detecting the polyp is only, available when the polyp is no longer depicted, creating a situation where an indication of a detected polyp is provided when the presented image does not present the polyp. It is noted that when frame number i+2 is available for presentation, the frame must be presented as soon as it is available (e.g., in real time and/or immediately) since a delay in the presentation of frames is unacceptable from the clinical and/or regulatory point of view, for example, may lead to injury in an attempt to remove the imaged polyp. Tracking based on features, which is computationally efficient leading to rapid processing in comparison to neural network based processing (e.g., less than 10 ms on typical PC with 17 Intel processor), is used, as described herein, to transform the ROI depicting the polyp detected in frame i to the location in frame i+2. The transformed location is the location that is presented on the display with frame number i±2. Optionally, the bounding box of the ROI (e.g., only the bounding box of the ROI) is transformed to the i+2 frame, since the contour transformation may be more inaccurate due to different 3D positions influences which are not necessarily taken into account in the 2D transformation. It is noted that the i+2 frame is an example, and not necessarily limiting, as other examples may be used, for example, i+1, i+3, i+4, i+5, and greater.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
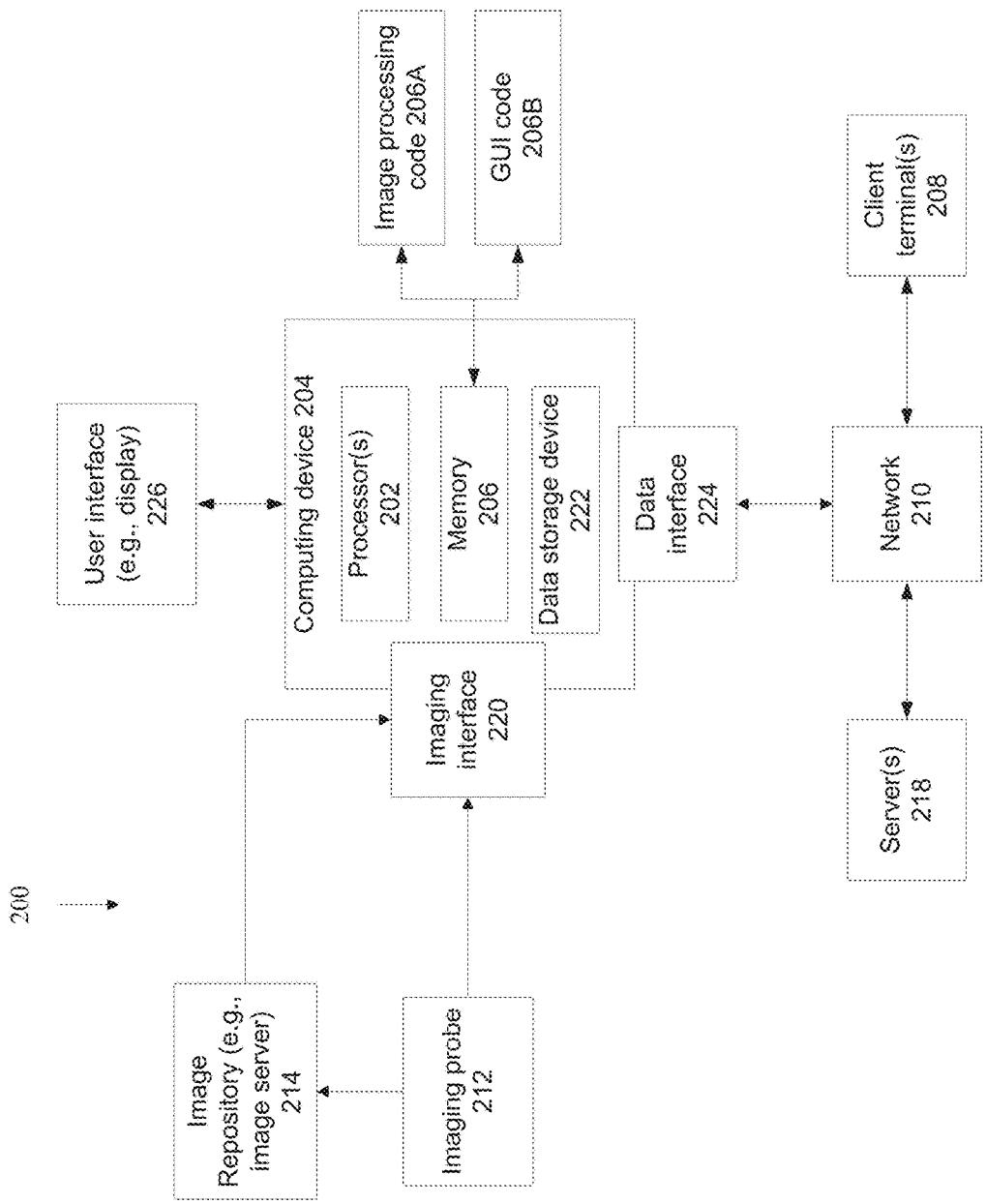
FIG. 2 is a is a block diagram of components of a system for processing images acquired by a camera located on an endoscope within a colon of a target patient, in accordance with some embodiments of the present invention.

Reference is now made to FIG. 1, which is a flowchart of a method for processing images acquired by a camera located on an endoscope within a colon of a target patient, for tracking polyp(s), tracking motion of the camera, mapping locations of polyp(s), computing coverage of the inner surface of the colon, tracking amount of time spent at different parts of the colon, and/or for computing volume of the polyps(s), in accordance with some embodiments of the present invention. Reference is also made to FIG. 2, which is a block diagram of components of a system 200 for processing images acquired by a camera located on an endoscope within a colon of a target patient, tracking polyp(s), tracking motion of the camera, mapping locations of polyp(s), computing coverage of the inner surface of the colon, tracking amount of time spent at different parts of the colon, and/or for computing volume of the polyps(s), in accordance with some embodiments of the present invention. System 200 may implement the acts of the method described with reference to FIG. 1, optionally by a hardware processor(s) 202 of a computing device 204 executing code instructions stored in a memory 206.

An imaging probe 212, for example, a camera located on a colonoscope, captures images within a colon of a patient, for example, obtained during a colonoscopy procedure. The colon images are optionally 2D images, optionally color images. The colon images may be obtained as a streamed video, and/or sequence of still images. Captured images may be processes in real time, and/or processed offline (e.g., after the procedure is completed).

Captured images may be stored in an image repository 214, optionally implemented as an image server, for example, a Picture Archiving and Communication System (PACS) server, and/or an electronic health record (EHR) server. Image repository may be in communication with a network 210.

A computing device 204 receives the captured images, for example, directly in real time from imaging probe 212, and/or from image repository 214 (e.g., in real time, or off-line). Real time images may be received during the colonoscopy procedure, for guiding the operator, as described herein. The captured images may be received by computing device 204 via one or more imaging interfaces 220, for example, a wire connection (e.g., physical port, for example, output from imaging probe 212 is plugged into the imaging interface via a connecting wire), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)). Computing device 204 analyzes the captured image as described herein, and generates instructions for dynamically adjusting a graphical user interface presented on a user interface (e.g., display) 226, for example, elements of the GUI are injected as an overlay over the captured images and presented on the display, as described herein.

Computing device 204 may be implemented as, for example, a dedicate device, a client terminal, a server, a virtual server, a colonoscopy workstation, a gastroenterology workstation, a virtual machine, a computing cloud, a mobile device, a desktop computer, a thin client, a Smartphone, a Tablet computer, a laptop computer, a wearable computer, glasses computer, and a watch computer. Computing 204 may include an advanced visualization workstation that sometimes is add-on to a gastroenterology and/or colonoscopy workstation and/or other devices for enabling the operator to view the GUI created from a processing of the colonoscopy images, for example, real time presentation of directing arrows towards polyps not currently seen on the image and/or colon map presenting 2D and/or 3D locations of polyps, and/or other features described herein.

Computing device 204 may include locally stored software that performs one or more of the acts described with reference to FIG. 1 and/or may act as one or more servers (e.g., network server, web server, a computing cloud, virtual server) that provides services (e.g., one or more of the acts described with reference to FIG. 1) to one or more client terminals 208 (e.g., client terminal used by a user to view colonoscopy images, for example, a colonoscopy workstation that includes a display presenting the images captured by the colonoscope 212, a remotely located colonoscopy workstation, PACS server, remote EHR server, remotely located display for remote viewing of the procedure such as by medical students). Services may be provided over network 210, for example, providing software as a service (SaaS) to the client terminal(s) 208, providing an application for local download to the client terminal(s) 208, as an add-on to a web browser and/or a colonoscopy application, and/or providing functions using a remote access session to the client terminals 208, such as through a web browser, application programming interface (API), and/or software development kit (SDK), for example, for injection of GUI elements into colonoscopy images, and/or presenting the colonoscopy images within the GUI.

Different architectures of system 200 may be implemented. For example:

Computing device 204 is connected between imaging probe 212 and display 226, for example, components of a colonoscopy workstation. Such implementation may be used for real time processing of the images captured by the colonoscope during the colonoscopy procedure, and real time presentation of the GUI described herein on display 226, for example, injecting the GUI elements and/or presenting the images within the GUI, for example, presenting direction arrows to currently unseen polyps and/or presenting a colon map depicting 2D and/or 3D location of polyps and/or other features described herein. In such implementation, computing device 204 may be installed for each colonoscopy workstation (e.g., includes imaging probe 212 and/or display 226).

Computing device 204 acts as a central server, providing services to multiple colonoscopy workstation such as client terminals 208 (e.g., includes imaging probe 212 and/or display 226) over network 210. In such implementation, a single computing device 204 may be installed to provide services to multiple colonoscopy workstations.

Computing device 204 is installed as code on an existing device such as server 218 (e.g., PACS server, EHR server) to provide local off-line processing for the respective device, for example, off-line analysis of colonoscopy videos captured by different operators and stored in the PACS and/or EHR server. Computing device 204 may be installed on an external device in communication over network 210 with server(s) 218 (e.g., PACS server, EHR server) to provide local off-line processing for multiple devices.

Client terminal(s) 208 may be implemented as, for example, as a colonoscopy workstation that may include imaging probe 212 and display 226, a desktop computer (e.g., running a viewer application for viewing colonoscopy images), a mobile device (e.g., laptop, smartphone, glasses, wearable device), and remote station server for remote viewing of colonoscopy images.

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, memory 206 may store code 206A that implement one or more acts and/or features of the method described with reference to FIG. 1, and/or GUI code 206B that generates the instructions for presentation within the GUI and/or that presents the GUI described herein based on the instructions (e.g., injection of GUI elements into the colonoscopy images, an overlay of GUI elements on the images, presentation of the colonoscopy images within the GUI, and/or presentation and dynamic update of the colon map described herein).

Computing device 204 may include a data storage device 222 for storing data, for example, the received colonoscopy images, the colon map, and/or the processed colonoscopy images presented within the GUI. Data storage device 222 may be implemented as, for example, a memory, a local hard-drive, a removable storage device, an optical disk, a storage device, and/or as a remote server and/or computing cloud (e.g., accessed over network 210).

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated imaging processing code, updated GUI code, and/or to obtain image for off-line processing.

It is noted that imaging interface 220 and data interface 224 may be implemented as a single interface (e.g., network interface, single software interface), and/or as two independent interfaces such as software interfaces (e.g., as APIs, network ports) and/or hardware interfaces (e.g., two network interfaces), and/or combination (e.g., single network interface, and two software interfaces, two virtual interfaces on a common physical interface, virtual networks on a common network port). The term/component imaging interface 220 may sometimes be interchanged with the term data interface 224.

Computing device 204 may communicate using network 210 (or another communication channel, such as through a direct link (e.g., cable, wireless) and/or indirect link (e.g., via an intermediary computing device such as a server, and/or via a storage device) with one or more of: server(s) 218, imaging probe 212, image repository 214, and/or client terminal(s) 208, for example, according to different architectural implementations described herein.

Imaging probe 212 and/or computing device 204 and/or client terminal(s) 208 and/or server(s) 218 include or are in communication with a user interface 226 that includes a mechanism designed for a user to enter data (e.g., mark a polyp for removal) and/or view the GUI including the colonoscopy images, direction arrows, and/or colon map. Exemplary user interfaces 226 include, for example, one or more of, a touchscreen, a display, a keyboard, a mouse, augmented reality glasses, and voice activated software using speakers and microphone.

At 100, the endoscope is inserted and/or moved within the colon of the patient. For example, the endoscope is advanced forward (i.e., from rectum to cecum), retraced (e.g., from cecum to rectum), and/or the orientation of at least the camera of the endoscope is adjusted (e.g., up, down, left, right), and/or the endoscope is left in place.

It is noted that the endoscope may be adjusted based on the GUI, for example, manually by the operator and/or automatically by the user, for example, the user may adjust the camera of the endoscope according to the presented arrow to re-capture a polyp that moved out of the images.

At 102, an image is captured by the camera of the endoscope. The image is a 2D image, optionally in color. The image depicts the inside of the colon, and may or may not depict a polyp.

Images may be captured as a video stream. Individual frames of the video stream may be analyzed.

Images may be analyzed individual, and/or as a set of sequential images, as described herein. Each image in the sequence may be analyzed, or some intermediate images may be ignored, optionally a predefined number, for example, every third image is analyzed, with the intermediate two images being ignored.

Optionally, one or more polyps depicted in the image are treated. The polyps may be treated via the endoscope. The polyps may be treated by surgical removal thereof, for example, for sending to a pathology lab. Polyps may be treated by ablation.

Optionally, treated polyps are marked, for example, manually by the physician (e.g., making a selection using the GUI, by pressing a "polyp removed" icon), and/or automatically by code (e.g., detects movement of the surgical excision device). Marked treated polyps may be tracked and/or presented on the colon map presented in the GUI, as described herein.

At 104, the image is fed into a detection neural network that outputs an indication of whether a polyp is depicted in the image (or not). The detection neural network may include a segmentation process that identifies the location of the detected polyp in the image, for example, by generating a boundary box and/or other contour that delineates the polyp in the 2D frame.

An exemplary neural network based process for detection of polyps is the Automatic Polyp Detection System (APDS) described with reference to International Patent Application Publication No. WO 2017/042812 "A SYSTEM AND METHOD FOR DETECTION OF SUSPICIOUS TISSUE REGIONS IN AN ENDOSCOPIC PROCEDURE", by the same inventor as the present application.

The automated polyp detection process implemented by the detection neural network may be executed in parallel to, and/or independently of features 106-114, for example, on the same computing device and/or processor(s) and/or on another real-time connected computing device and/or platform that is connected to the computing device executing the features described with reference to 106-114.

When the output of the neural network is computed and provided for a previous endoscopic image that is sequentially earlier than the respective endoscopic image, and the tracked location of the region depicting the polyp(s) within the respective endoscopic image (i.e., as described with reference to 106) is at a different location than the region outputted by the neural network for the previous endoscopic image, the augmented image is created for the respective endoscopic image based on the computed tracked location of the polyp. Such situation may arise when the frame rate of the images is faster than the processing rate of the detection neural network. The detection neural network completes processing of an image after one or more sequential images have been captured. If the results of the detection neural network are used in such a case, the computed polyp location for the older images may not necessarily reflect the polyp location for the current image.

Optionally, one or more endoscopic images of a sequential sub-set of the endoscopic images including the respective endoscopic image and one or more images sequentially located earlier than the respective endoscopic images (e.g., captured prior to the respective endoscopic image) that depict the tracked ROI (as described with reference to 106) are fed into the detection neural network. The sequential sub-set of images may be fed into the detection neural network in parallel to the tracking processing (as described with reference to 106). Alternatively, the sub-set of images are first processed by the tracking process as described with reference to 106. One or more of the post-processed images may be translated and/or rotated one to create a sub-set of endoscopic images where the region depicting the polyp(s) (e.g., ROI) detected by the tracking process is at a same approximate position in all of the images, for example, at the same pixel locations on the display for all images. The processed sequential-sub set of images are fed into the detection neural network for outputting the current region delineating the polyp(s). The image may be augmented with the region detected by the detection neural network.

Alternatively or additionally, the computed tracked location of the region depicting the polyp within the image(s), and/or the output of the tracking process (e.g., the 2D transformation matrix between successive frames) as described with reference to 106 is fed into the detection neural network. The tracked location and/or 2D transformation matrix may be fed into the neural network when the tracked location of the polyp is within the image, or when the tacked location of the polyp is located externally to the image. The tracked location may be fed into the neural network alone, or in addition to one or more images (e.g., the current image and/or a previous image(s)). The output of the tracking process (e.g., the tracked location and/or 2D transformation matrix) may be used by the neural network process, for example, for improved accuracy of correlation between the detection of polyps in successive frames. The output of the tracking process may increase the confidence of the neural network based polyp detection process (e.g., when the tracked polyp was detected in previous frames) and/or may reduce the cases of false positive detection.

Optionally, in case of mismatch between the tracked location of the polyp (e.g., ROI depicting the polyp) as computed based on 106, and output of the detection neural network, the location of the neural network is used. The location outputted by, the neural network is used to generate instructions for creating the augmented image augmented with an indication of the location of the polyp. The location of the polyp outputted by the neural network may be considered as more reliable than the tracked location computed as described with reference to 106, although the location computed by tracking is computationally more efficient and/or may be performed in a shorter time than processing by the neural network.

Optionally, the 3D reconstruction of the 2D image, as described with reference to 108 is fed into the detection neural network in alone and/or combination with 2D image for outputting the indication of the region depicting the at least one polyp.

Referring now back to FIG. 1, at 106, a location of a region (e.g., ROI) depicting one or more polyps is tracked within the current endoscopic image relative to one or more previous endoscopic images.

It is noted that the camera movement (e.g., orientation, forward, reverse) is indirectly tracked by tracking the movement of the ROI between images, since the camera is moving while the polyps remain stationary at their position within the colon. It is noted that some movement of the ROI between frames may be due to peristalsis and/or other natural motion of the colon itself, independently of whether the camera is stationary or moving.

Optionally, the location is tracked in 2D. The polyp may be tracked by tracking the ROI that delineates the polyp. The ROI and/or polyp may be detected in one or more previous images by the detection neural network of feature 104.

The location of the polyp is tracked even when the polyp is not depicted in the current image, for example, the camera is positioned such that the polyp is no longer present in the image captured by the camera.

Optionally, a vector is computed from a location within the current image to the location of the polyp and/or ROI located externally to the current image. The vector may be computed, for example, from the location of the ROI on the last (or earlier) image that depicted the ROI, from the middle of the screen, from the middle of a quadrant of the screen closest to the location of the external ROI, and/or from another region of the image closest to the location of the external ROI (e.g., a predefined distance away from the location at the border of the image closest to the location of the external ROI).

The indication of the vector may depict a direction and/or orientation for adjustment of the endoscopic camera for capturing another endoscopic image depicting the region of the image.

Optionally, the tracking algorithm is feature based. The features may be extracted from an analysis of the endoscopic image. Features may be extracted based on the Speed Robust Features (SURF) extraction approaches, described with reference to Bay, Herbert, Tinne Tuytelaars, and Luc Van Gool. "*Surf: Speeded up robust features.*" *European conference on computer vision*. Springer, Berlin, Heidelberg, 2006. The tracking of the extracted features may be performed in two dimensions (2D) between successive images (it is noted that one or more intermediate images between the analyzed may be skipped, i.e., ignored). Features may be matched, for example, based on the K-d tree approach described with reference to Silpa-Anan, Chanop, and Richard Hartley. "*Optimised KD-trees for fast image descriptor matching.*" (2008): 1-8. The k-d tree approach may be selected, for example, based on the observation that the main movement in colonoscopy procedure is the endoscopic camera movement in the colon. Features may be matched according to their descriptors, between successive images. The best homography may be estimated, for example, using the Random Sample Consensus (RANSAC) approach, described with reference to Vincent, Etienne, and Robert Laganiere. "*Detecting planar homographies in an image pair.*" *ISPA* 2001. *Proceedings of the 2nd International Symposium on Image and Signal Processing and Analysis. In conjunction with 23rd International Conference on Information Technology Interfaces (IEEE Cat., IEEE,* 2001), by computing the 2D affine transformation matrix, as described with reference to Agarwal, Anubhav, C. V. Jawahar, and P. J. Narayanan. "*A survey of planar homography estimation techniques.*" *Centre for Visual Information Technology, Tech. Rep. IIT/TR/2005/12*(2005) (and its closest 2D geometry transformation matrix) of the camera movement from frame to frame.

A certain Region Of interest (ROI) may be tracked, optionally a bounding box denoting location of one or more polyp therein. The location of the ROI is tracked while the ROI moves out of the image (e.g., video) frame. The ROI may be tracked until the ROI returns back (i.e., is again depicted) in the current frame. The ROI may be continuously tracked beyond the image frame borders, for example, based on a tracking coordinate system that is defined externally to the image frames.

During the time interval between when a polyp is detected (e.g., automatically, by code, and/or manually by the operator) until the time the camera movement is stopped (e.g., when the operator focuses attention on the detected polyp), the polyp may moves out of the frame. Instructions may be generated for presenting an indication of where the polyp (or ROI associated with the polyp) is currently located externally to the presented image. For example, by augmenting the current image(s) with a presentation of a directional arrow. The arrow points to where the operator should move the camera (i.e., the endoscope tip) in order to get the polyp (or ROI of the polyp) depicted back again in the new frame(s).

Figure 3:
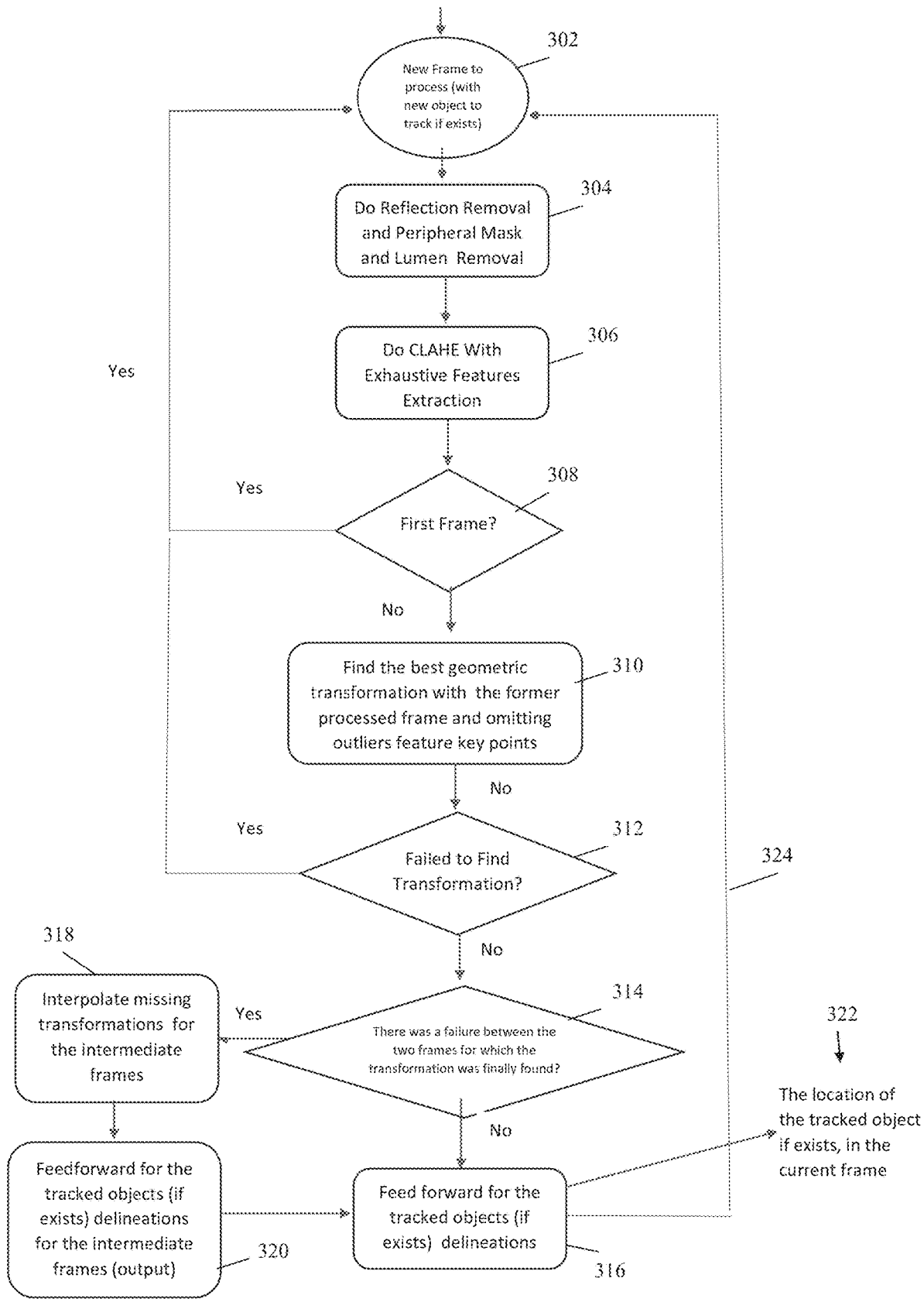
FIG. 3 is a flowchart of a process for tracking a location of a region depicting one or more polyps within a respective endoscopic image relative to one or more previous endoscopic images, in accordance with some embodiments of the present invention.

Optionally, the arrow (or other indication) may be presented until the camera moves too far (e.g., greater than a defined threshold) from the tracked polyp. The predefined threshold may be defined, for example, as the distance of the polyp's new location from the center of the current frame being more than 3 times the length, in pixels, of the diagonal of the frame, or other values, Reference is now made to FIG. 3, which is a flowchart of a process for tracking a location of a region depicting one or more polyps within a respective endoscopic image relative to one or more previous endoscopic images, in accordance with some embodiments of the present invention.

At 302, a new (i.e., current) image, optionally a new frame of a video captured by the camera of the colonoscope is received. The image may or may not depict one or more polyps which are being tracked.

At 304, the irrelevant or misleading portions are removed from the image for example, the periphery which is not part of the colon, the lumen which is the dark area in the colon image from which the light does not return to the camera (e.g., representing the far central part of the colon)), and/or the reflections which are inconsistent in successive frames since they are dependent on the light source which moves with the camera.

At, 306 the contrast limited adaptive histogram equalization (CLAHE) process (e.g., described with reference to Reza, Ali M. "*Realization of the contrast limited adaptive histogram equalization (CLAHE) for real-time image enhancement.*" *Journal of VLSI signal processing systems for signal, image and video technology* 38.1 (2004): 35-44) and/or other process is implemented for enhancing the image. The speed robust features (SURF) approach is implemented for extracting the features, optionally right after the CLAHE (e.g., without significant delay).

At 308, when the current frame is the first frame of the sequence and/or the first frame in which a polyp is detected, 302 is iterated for obtaining the next frame. When the current frame is not the first frame, then 310 is implemented to process the current frame with the former frame that was processed in a previous iteration.

At 310 a geometry matrix is computed, optionally based on homography, for the camera movement between the two successive frames (e.g., frame number denoted i and frame number denoted i+n, namely a jump of n frames between two frames which are processed together).

At 312, when no transformation is found, then the next image (e.g., frame) in the sequence is processed (by iterating 302) with the former (i.e., current) frame (i.e., when frames i and i+n couldn't match then an attempt is made to try to match frames i and i+n+1), otherwise 314 is implemented.

At 314, when there is a failure to find a transformation between the former two or more frames (i.e., the location of the tracked object (i.e., polyp) in the last frame is not and/or cannot be computed) then 318 is implemented, otherwise when the location of the polyp is computed then 316 is implemented.

At 316, when an object (i.e., polyp) is identified in the image for tracking, then the region which is being tracked is fed forward to the current frame according to the transformation that was found in 310. 322 is implemented for generating instructions for depicting the object (i.e., polyp) in the current frame, for example, by a visual marking such as a box.

Alternatively, at 318, the transformations for intermediate frames for which transformation was not found are interpolated according to the last transformation that was found between the two frames before and after the intermediate frames.

At 320, when there is an object (i.e., polyp) which is being tracked then the region which is being tracked is fed forward to the intermediate frames according to the interpolated transformations that were found in 318. 322 is implemented for generating instructions for depicting the object (i.e., polyp) in these frames. 316 may be implemented for depict the object (i.e., polyp) also on the current frame.

At 324, the process is iterated for tracking when the object (i.e., polyp) is out of the frame. The next frame to process may be in jump steps, for example, two or three or more frames are ignored until a new frame is processed, or alternatively every frame is processed.

Figure 4:
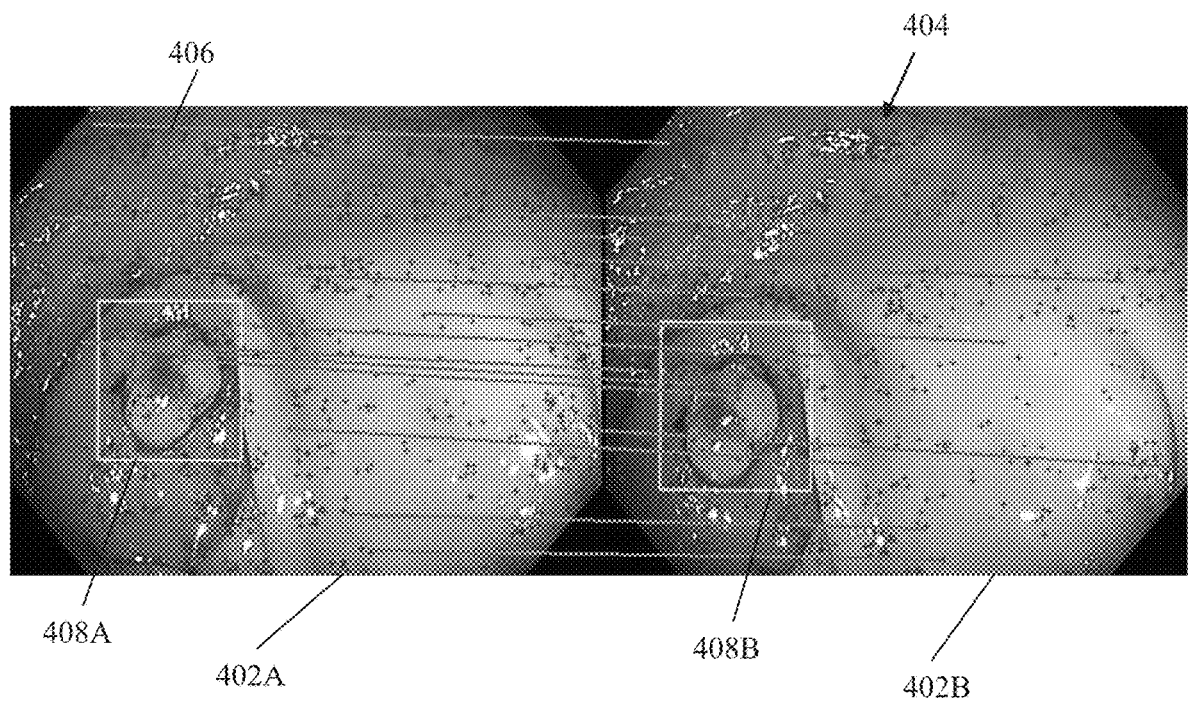
FIG. 4 is a schematic depicting an example of a feature-based K-D tree match between two successive images, in accordance with some embodiments of the present invention.

Reference is now made to FIG. 4, which is a schematic depicting an example of a K-D tree match between two successive images 402A-B that were matched together by corresponding features (features shown as plus signs, one is labeled 404, matching features are marked using lines, one is show as 406), for tracking a polyp within a region 408A-B, in accordance with some embodiments of the present invention. Image 402A may be denoted as frame number i. Image 402B may be denoted as frame number i+3. Region E08A denotes the original boundary box of the region, and region E08B denotes the transformation of E08A, according to the transformation matrix calculated by the homograph); of the matches between the key points, as described herein.

Figure 5:
FIG. 5 is a geometric transformation matrix between frames of FIG. 4, in accordance with some embodiments of the present invention.

Reference is now made to FIG. 5, which is a geometric transformation matrix 502 between frames 402A-B of FIG. 4, in accordance with some embodiments of the present invention.

Figure 6:
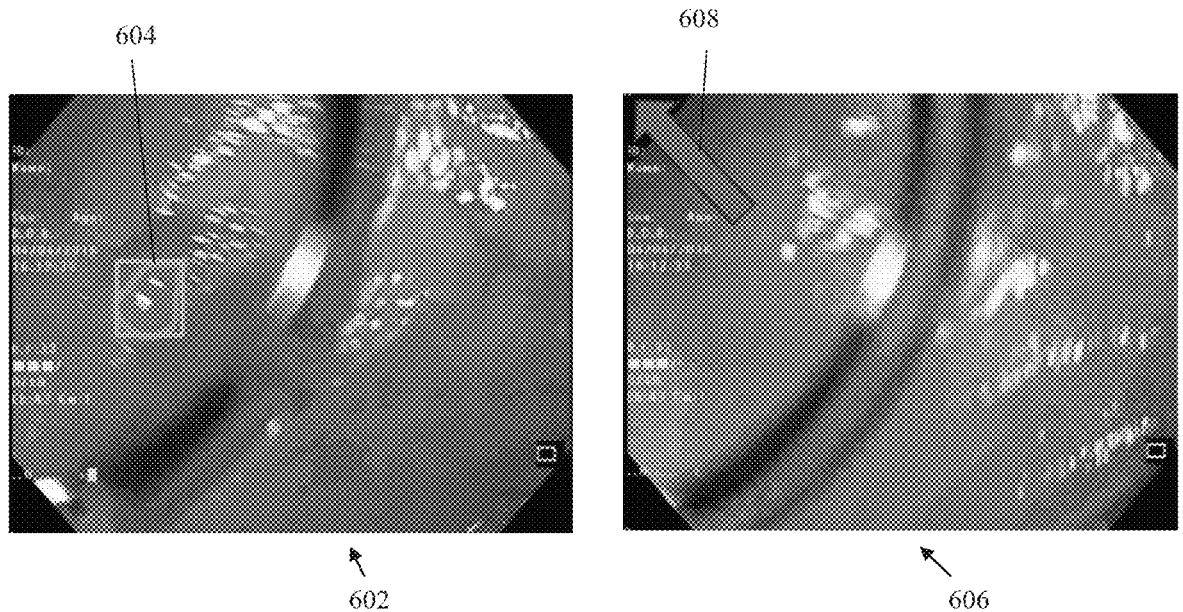
FIG. 6 is a schematic depicting an ROI of a bounding box denoting a detected polyp which is being tracked, and a sequentially later schematic where the tracked bounding box is no longer depicted within the image, which is augmented with a presentation of an arrow indicating a direction in which to move the camera in order to re-depict the ROI of the polyp in the captured image, in accordance with some embodiments of the present invention.

Reference is now made to FIG. 6, is a schematic 602 depicting an ROI 604 of a bounding box denoting a detected polyp which is being tracked, and a sequentially later schematic 606 (e.g., two frames later) where the tracked bounding box is no longer depicted within the image, which is augmented with a presentation of an arrow 608 indicating a direction in which to move the camera in order to re-depict the ROI of the polyp in the captured image, in accordance with some embodiments of the present invention.

Figure 7:
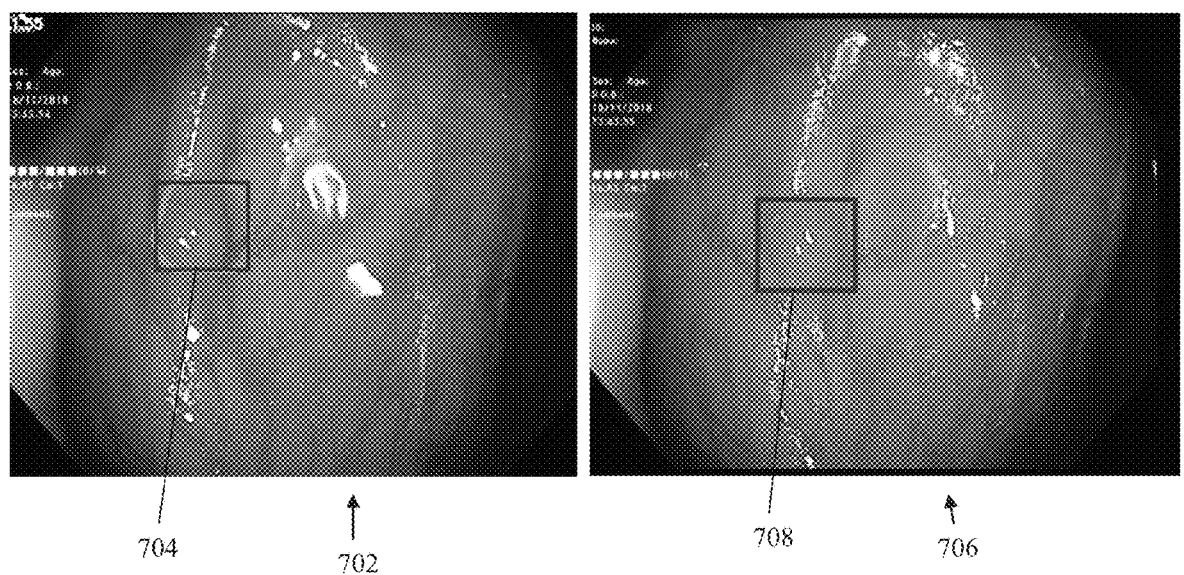
FIG. 7 is a schematic depicting a detected polyp, and a sequentially later frame depicting the tracked polyp computed using the transformation matrix described herein, in accordance with some embodiments of the present invention.

Reference is now made to FIG. 7, is a schematic 702 depicting a detected polyp 704, and a sequentially later frame (i.e., three frames later in time) 706 depicting the tracked polyp 708 computed using the transformation matrix described herein, in accordance with some embodiments of the present invention.

Reference is now made back to FIG. 1. At 108, a 3D reconstruction is computed for the current 2D image. The 3D reconstruction may define 3D coordinate values for pixels of the 2D image.

Optionally, a 3D reconstruction neural network is trained for outputting a 3D image from an input of a 2D image. The trained 3D reconstruction neural network generates more accurate 3D images from 2D images in comparison to a 3D reconstruction process (e.g., a standard 3D reconstruction process) alone. The 3D reconstruction process is a different process than the 3D reconstruction neural network. The 3D reconstruction process may be based on standard 3D reconstruction processes, for example, that compute the 3D reconstruction using only a single 2D image. The 3D reconstruction neural network is trained using a training dataset of 2D images as captured by the colonoscopic camera, and corresponding 3D images created from the 2D images by the 3D reconstruction process. The 2D image is designated as input and the reconstructed 3D image is designated as ground truth.

Optionally, a process for computing the 3D reconstruction of the current 2D image is based on a 3D neural network neural network that outputs the 3D reconstruction. The 3D reconstruction neural network may be trained using a training dataset of pairs of 2D endoscopic images defining input images and corresponding 3D coordinate values computed for pixels of the 2D endoscopic images computed by a 3D reconstruction process defining ground truth. The neural network, which may be trained on a large training dataset (e.g., on the order of 10000-100000 or 100000-1000000) may provide increased accuracy relative to the 3D reconstruction process alone.

The neural network may be trained using pairs of a colon in-vivo images captured by the endoscope camera (denoted as the input) and corresponding 3D values as estimated by a 3D reconstruction process (denoted as the ground truth). The 3D values may be 3D coordinates computed for 2D pixels of the image. The 3D reconstruction process may be trained using a large dataset (e.g., at least 100,000 images of the colon from at least 100 different colonoscopy videos, or other smaller or larger values).

An exemplary process for 3D reconstruction of the 2D colon images is now described: The 3D geometry of the partial interior surface region of the colon may be reconstructed for each frame, for example, using the Shape from Shading (SfS) process described with reference to Zhang, Ruo, et al. "*Shape-from-shading: a survey.*" *IEEE transactions on pattern analysis and machine intelligence* 21.8 (1999): 690-706 and/or Prasath, VB Surya, et al. "*Mucosal region detection and 3D reconstruction in wireless capsule endoscopy videos using active contours.*" 2012 *Annual International Conference of the IEEE Engineering in Medicine and Biology Society. IEEE*, 2012. Motion parameters of the camera may be computed, for example, based on the Shape from Motion (SfM) process described with reference to Szeliski, Richard, and Sing Bing Kong. "*Recovering 3D shape and motion from image streams using nonlinear least squares.*" *Journal of Visual Communication and Image Representation* 5.1 (1994): 10-28. The 3D location of one or more feature points may be computed, optionally for integrating the partial surfaces reconstructed by the SfS algorithm. The SfS algorithm handles the moving local light and light attenuation. The real situation during endoscopy inside the human organ may be mimicked. One exemplary advantage of the 3D reconstruction process described herein in comparison with other SfS based processes is that the 3D reconstruction process described herein may compute an unambiguous reconstructed surface for each frame. The 3D reconstructions process may delete the non-Lambertian (e.g., the more specular reflection) regions using a threshold on intensity to make the SfS process work for the other regions. The SfS process implemented by inventors (described with reference to Prados, E., Faugeras, O.: *Shape from shading: a well-posed problem?. IEEE Conference on Computer Vision and Pattern Recognition,* 870-877 (2005)) creates unambiguous surfaces. The unambiguous surfaces may be computed by taking into account $1/r^2$ light attenuation, and/or assuming that the spot light source is attached at the center of the projection of the Camera so the image brightness is denoted as $$E = \alpha I \frac{\cos\theta}{r^2},$$

where $\theta$ denotes the angle between the surface normal and the incident light, a denotes the albedo, and r denotes the distance between the light source and the surface point. The 3D reconstruction process described herein may integrate partial surfaces obtained from different frames using the motion information obtained by the SfM process. Inhomogeneous regions may be identified as feature points. The features may be used by the SfM process for estimating the extrinsic parameters of the camera for each frame, for example, as described with reference to Kaufman A., Wang (2008) *3D Surface Reconstruction from Endoscopic Videos*. In: Linsen L., Hagen H., Hamann B. (eds) *Visualization in Medicine and Life Sciences. Mathematics and Visualization.* Springer, Berlin, Heidelberg. The computed information provides enhanced accuracy for the integration of the partial surface of various frames as compared with ICP (Iterative Closest Points) algorithms (e.g., as described with reference to Kaufman A., Wang J. (2008) *3D Surface Reconstruction from Endoscopic Videos*. In: Linsen L., Hagen H., Hamann B. (eds) *Visualization in Medicine and Life Sciences. Mathematics and Visualization.* Springer, Berlin, Heidelberg).

The described 3D reconstruction process applied to colonoscopy video frames, yielded according to Kaufman A., Wang J. (2008) *3D Surface Reconstruction from Endoscopic Videos*. In: Linsen L., Hagen H., Hamann B. (eds) *Visualization in Medicine and Life Sciences. Mathematics and Visualization.* Springer, Berlin, Heidelberg, an average re-projection error, for selected feature point, of 0.066 pixel.

The standard 3D process described herein may be used to compute the estimation of the 3D reconstruction of the colon for each 2D frame. The 2D frames and corresponding calculated ground truth (i.e., the 3D reconstructed 3D values for the 2D frames) may be split to creating a training dataset (e.g., 70% of the data) and testing a dataset (e.g., 30% of the data). A Convolutional Neural Network (CNN), for example, based on an implementation which resembles encoder decoder architecture (e.g., as described with reference to Shan, Hongming, et al. "*3-D convolutional encoder-decoder network for low-dose CT via transfer learning from a 2-D trained network.*" *IEEE transactions on medical imaging* 37.6 (2018): 1522-1534) may be trained and tested by the training and validation datasets in order to be robust enough to predict for each 2D frame its 3D reconstruction.

In an exemplary architecture, the encoder and decoder part of the 3D reconstruction CNN may be built from 2D convolutional layers. The last layer may be multiplied 3 times to predict the 3D coordinate value for each pixel of the input image. The 3D reconstruction CNN may be used in real time to predict 3D values of each pixel in each 2D frame of the colon surface in the colonoscopy video. The CNN, which is trained on data outputted by the 3D reconstruction process, optionally using a large number of processed 2D images (e.g., on the order of 100000 or more or less) may be more robust and/or more accurate than the 3D reconstruction process alone.

Figure 8:
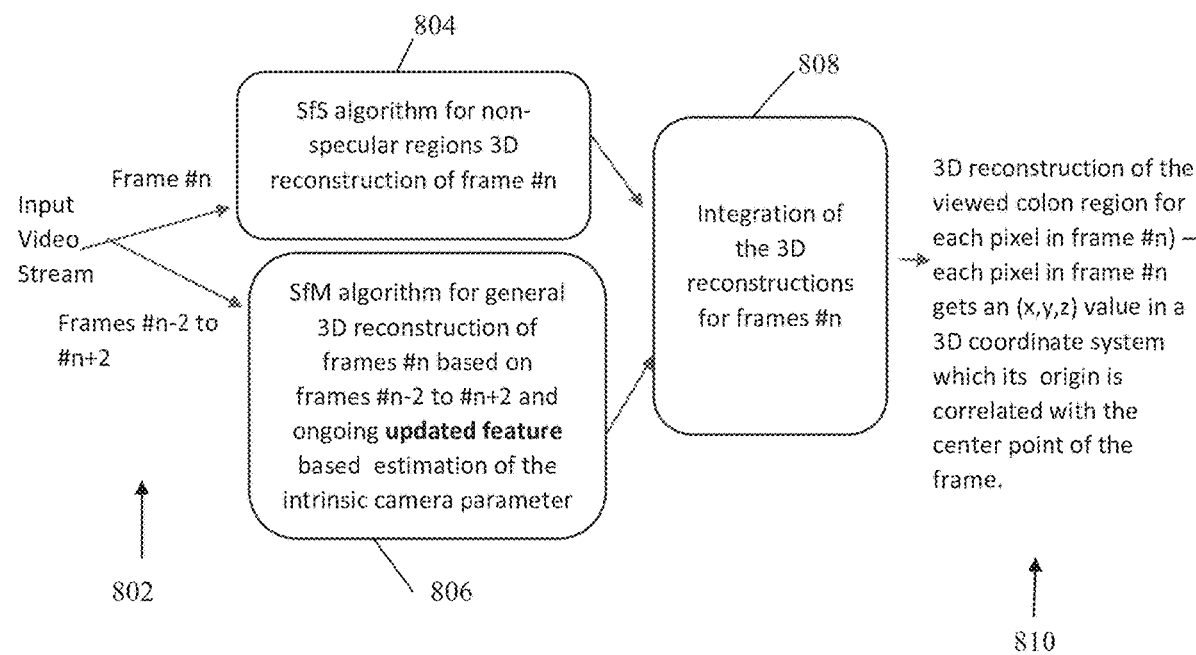
FIG. 8 is a flowchart of a process for 3D reconstruction of 2D images captured by a camera within the colon of the patient, in accordance with some embodiments of the present invention.

Reference is now made to FIG. 8, which is a flowchart of a process for 3D reconstruction of 2D images captured by a camera within the colon of the patient, in accordance with some embodiments of the present invention. The 3D reconstructions may be defined as ground truth values, in association with the 2D images defined as input values, for creation of a training dataset for training a 3D reconstruction neural network, as described herein.

At 802, the images are provided, optionally as a video stream of frames.

At 804, the current frame, denoted n, is processed. Optionally, a SfS process for non-specular regions is used for computing the 3D reconstruction of frame n.

At 806, multiple images, including images acquired before and after the current image are processed. Frames may be denoted as n−2 to n+2, or other numbers may be used. The SfM process may be used to compute a general 3D reconstruction of frames #n based on frames #n−2 to #n+2 and ongoing updated features based estimation of the intrinsic camera parameter.

At 808, the 3D reconstructions computed in 104 and 106 are integrated for frame n.

At 810, the 3D reconstruction is provided for each pixel in 2D frame #n, denoting the viewed colon region. Each pixel in 2D frame #n is assigned a (x,y,z) value in a 3D coordinate system. The origin of the 3D coordinate system may be correlated with the center point of the frame.

An exemplary data flow in of a 3D reconstruction CNN is now described. At a first phase denoted, successive 2D frames (i.e., an odd number at least 3, the number of successive input frames denoted n) are fed into the 3D CNN and goes through a layer of 3D convolutional kernels (n\*3\*3). The first layer is designed for processing all the 3 color channels of the 2D frame by being duplicated 3 times. The flow of data continues through a Batch Normalization and Relu layers, and a Max Pooling Layer which reduces the size of the output by 2 in each of frame dimensions. The data flow through an additional four group of layers, but with 2D convolution kernels, which represent encoder part of the 3D CNN. The data flow continues through an additional four groups of layers with 2D convolutions, but with up-sampling layer instead of the max pooling layer, and then through a fifth layer which is duplicated three times, which represent the encoder portion of the CNN. The output is at the same resolution as the input 2D frames. Three values are outputted for each 2D pixel which are the pixels (x,y,z) 3D coordinates value of the 2D pixel.

Optionally, the computed 3D values of the pixels of the 2D frame may be fed into the polyp detection process described with reference to 104 (e.g., the APDS detection process). The computed 3D values provide additional input (e.g., to the neural network) for detecting a polyp in the current frame and/or for determining the location of the polyp in the current frame. For example, the 3D values may information indicative of the flatness and/or the prominence of the colon tissue region which is suspected to be a polyp, relatively to its surroundings.

Reference is now made back to FIG. 1. At 110, the current 3D location of the polyp and/or endoscope is computed and/or tracked. The 3D location may be computed based on the output of the 3D reconstruction outputted by the 3D reconstruction neural network.

The 3D location may be computed based on a 3D rigid body transformation matrix that is computed between successive 2D endoscopic images based on the 3D coordinates of matched features extracted from the successive 2D endoscopic images and/or from the 3D reconstruction of the successive 2D endoscopic images. In other words, the 3D transformation matrix is computed for matched features using the 3D coordinates of the pixels corresponding to the features, for example, similar to the process described herein for tracking 2D images based on corresponding features between the 2D images, but using the 3D coordinates of the features rather than the 2D coordinates. The 3D body transformation matrix denotes movement of the endoscopic camera between the successive 2D endoscopic images. The current 3D location of the endoscopic camera is computed according to the 3D body transformation matrix in view of the respective 2D endoscopic image. A trajectory of the movement of the camera may be computed based on successive 3D transformation matrices. The trajectory of the movement of the camera may be presented in the colon map, as described herein.

Optionally, the 3D location of the detected polyp and/or endoscope is iteratively tracked according to computed 3D locations for multiple sequential images.

The 3D tracking process receives may be based on output of the 2D tracking process described with reference to 106 and/or on the 3D reconstruction process described with reference to 108. The feature extraction part and/or matching part may be implemented as described with reference to the 2D tracking on the 2D consecutive frames of the colonoscopy video. However it is noted that, the homography is calculated on the 3D values (x,y,z) of the extracted features (key points), rather on the 2D values. The 3D values are reconstructed by the 3D reconstruction process described herein, to find the best fitting 3D affine transformation. The 3D rigid body transformation which is the closest to the calculated 3D affine transformation is computed, for example, using the process described with reference to Yuan, Jie, et al, "*Application of Feature Point Detection and Matching in 3D Objects Reconstruction*", *PATTERNS* 2011: *The Third International Conferences on Pervasive Patterns and Applications*, 19-24. The 3D rigid body transformation matrix describes the 3D movement of the camera in the colon from frame to frame.

Reference is now made to FIG. 9, which is a flowchart depicting an exemplary 3D tracking process for tracking 3D movement of the camera, in accordance with some embodiments of the present invention.

At 1102, the matched features between frame n and the next analyzed sequential frame n±i are provided, for example, as output of the process executing 510 described with reference to FIG. 5.

At 1104, the computed 3D coordinate values of the matched features (key points) between frame n and n+i, are provided, optionally from the 3D reconstruction process (e.g., outputted by the 3D reconstructions neural network), as described herein.

At 1106, the 3D holography is computed according to the 3D coordinates values (1104) of the matched features (1102).

At 1108, the closest 3D rigid body transformation matrix is found.

At 1110, the affine 3D transformation matrix is computed.

At 1112, the 3D rigid body transformation matrix describing the movement of the camera from frame n to frame n+i is computed.

Reference is now made to FIG. 10, which is an example, of a 3D rigid body transformation matrix 1202, for tracking 3D movement of a colonoscopy camera, in accordance with some embodiments of the present invention.

Reference is now made back to FIG. 1. The 3D tracking algorithm enables to build a 3D trajectory of movements of the camera (e.g., during the colonoscopy procedure) is computed based on 3D tracking of the position of the camera. The 3D trajectory may be defined according to a 3D coordinate system, for example, the origin correlates to the camera location when tracking has been started (e.g., when the scope just entered to the colon for example, the point [0,0,0] in the 3D coordinate system at which the first, inside the colon, frame's 3D values were reconstructed). The trajectory may be built by calculating the 3D position of the camera e.g., principal point thereof) for each new frame (and/or for multiple new frames, for example, between 1 to 25 new frames) relative to the 3D position of the camera for the last frame from which the 3D position was calculated. The calculation of the new 3D position may be derived (e.g., immediately, without significant delay, for example, during the time that the current frame is presented on the display until the next frame is presented) from the 3D rigid body transformation matrix between the two frames (e.g., multiplying the newly calculated transformation matrix with the former calculated 3D position of the camera).

Optionally, the 3D movement of the camera is tracked with respect to 3D location(s) of anatomical landmarks and/or 3D location(s) of previously detected polyps. Anatomical landmarks may be predefined and/or set by the operator, for example, location of hemorrhoids, location of a cecum, anatomical abnormalities, and/or portions of the colon (e.g., traverse, ascending). Polyps may be detected automatically and/or manually during forward advance of the camera for removal during reverse withdrawal of the camera.

At 112, the portion of the inner surface of the colon depicted in the image is computed, for example, each portion is defined as a third, a quarter, an eighth (or other divisions) of the circumference of the inner surface of the colon. Coverage of each portion may be dynamically computed in real time, for example, whether the current captured images depict the respective portion (e.g., mostly depict). Coverage may be computed for the whole (or part of) the colon as an aggregation of coverage of individual portions, for example, providing a result such as about 94% of the inner surface of the colon is covered, and/or about 6% of the inner surface of the colon has not been covered.

Optionally, an indication of a total amount of the inner surface depicted in images relative to an amount of non-depicted inner surface is computed by aggregating the portions covered during the spiral scanning motion relative to the portions not covered during the spiral scanning motion.

The portion of the inner surface of the colon depicted within the endoscopic image(s) may be computed, for example, based on an analysis of the 3D reconstruction of the image and/or based on an analysis of the image itself, for example, according to an identification of the location of the lumen within the image. The lumen may be identified, for example, as a region of pixels having intensity values below a threshold denoting darkness (i.e., of the lumen which does not reflect the light source back to the camera).

Optionally, multiple sequential images are aggregated to generate a single mosaic image. The portion of the inner surface of the colon may be computed for the single mosaic image and/or for individual images. The multiple sequential images may taken at different orientations of the camera, for example, as the camera is oriented clock-wise, anti-clock-wise, using an x-pattern, or other movements. The camera may remain still at the same location along a long axis of the colon, or may be moved at the same time as being oriented, for example, in a spiral pattern, for example, as the camera is being pushed forward and/or retracted.

Cumulative portions of the inner surface of the colon depicted within successive endoscopic images may be tracked per location. The portion of the inner surface of the colon may be computed per location in the colon, for different orientations of the camera, without displacing the camera forward or backwards (e.g., displacement is zero, or lower than a predefined threshold). When the camera is moved, the portion of the inner surface of the colon depicted in the captured images may be re-computed for each new location, for example, as the colonoscope is withdrawn from the colon. For example, Q1, Q2, Q3, Q4 as a set for the current location, and another set of Q1, Q2, Q3, Q4 for the new location. Alternatively, cumulative portions of the inner surface of the colon depicted within successive endoscopic images are tracked during the spiral movement of the camera. The portion of the inner surface of the colon depicted in the captured images may be re-computed in a spiral pattern as the camera is being moved, for example, the quarters are individually iterated for the spiral motion, for example, Q1, Q2, Q3, Q4, Q 1, Q2, Q3, Q4, Q1, Q2, Q3, Q4.

Optionally, each portion corresponds to a time window having an interval corresponding to an amount of time for covering the entire inner circumference during the spiral scanning motion, i.e., returning to the same arc location after a single spiral scan, i.e., completing about 360 degrees, or returning to the arc range defining the same quarter, i.e., after Q1 is completed, completing Q2, Q3 and Q4, and returning back to Q1. An indication of coverage of each portion may be updated as a correlation to the time window. For example, when all portions are continuously associated with an indication of coverage (e.g., all portions colored red or other color for adequate coverage), the operator is covering all portions adequately. Each portion may be associated with the indication of adequate coverage for a time interval corresponding to the time window, i.e., the portion is adequately covered until the current circumferential spiral ends, and needs to be adequately depicted in the new circumferential spiral. The operator may use the indication that all portions are adequately covered as a guideline during the continuous spiral scanning that the images of the colon are properly captured. When one of the indications of one of the portions changes to an indication of inadequate coverage, the operator may capture the respective portion in image(s).

The time window may be an estimate of the speed of spiral scanning motion, for example, based on clinical guidelines and/or based on physician practices, for example, about 2.5 seconds per quarter, or about 5 seconds per quarter, or other values per portion, or about 10 seconds or about 20 seconds per circumferential spiral scan, or other values. The time window may be dynamically computed and adjusted based on a real time measurement of the spiral scanning motion being performed by the operator. For example, when the operator stops the spiral scanning, for example, to focus in on a polyp, the time window is stopped, and resumed when the operator resumes the spiral scanning. When the operator slows down the spiral scanning rate, for example, the same operator or letting a student (e.g., resident) perform the scanning, the time window is increased accordingly. The real time speed of spiral scanning motion may be measured, for example, by an analysis of the captured images (e.g., tracking distances between matching extracted features in view of the frame capture rate), and/or by sensor(s) that sense motion of the colonoscope. An indication of adequate converge is generated when one or more image depicting mostly the respective portion is captured during the time window and/or another indication of inadequate coverage is generated when no images depicting mostly the respective portion are captured during the time window.

An indication of adequate coverage may be generated, for example, when at least 50%, or 60%, or 70%, or 80%, or 90%, or other intermediate or larger values, of the respective portion is depicted in the respective image. The threshold for determining the amount of the portion required in the respective image may be set, for example, based on the lens and the area of the internal surface of the colon depicted in the image.

Optionally, 3D values of the pixels in the tracked frames are integrated into one 31) coordinate system. A 3D panoramic (mosaic) image of the colon surface may be generated based on the single 3D coordinate system, for example, based on the process described with reference to Morimoto, Carlos, and Rama Chellappa. "*Fast 3D stabilization and mosaic construction.*" *cvpr. IEEE,* 1997. The mosaic image may be built continuously (e.g., when the endoscope is being pulled out of the colon).

For each frame included in the mosaic image, the lumen region (e.g., the center of the colon tube) may be detected, for example, by identifying dark pixels as pixels having intensity values below a threshold (e.g., below 20 or other values when the intensity range is 0-255), and for which the dark pixels have correlated 3D locations (or the 3D locations correlated to pixels in their close environment) which are the farthest from the camera position when the frame was captured.

Optionally, the location around the circumference of the inner surface of the colon covered by the current frame is computed. Optionally, the inner surface of the colon is divided, for example, into quarters. The quarter of the inner surface of the colon depicted by the current frame may be computed, for example, the first, second, third, or fourth quarter of the colon. The captured images may be aggregated into the mosaic image, for incrementally covering the quarters, optionally until the mosaic image depicts all four quarters, indicating that the entire circumference of the inner surface of the colon at the current location has been depicted in images.

The quarter(s) of the inner surface of the colon depicted in individual images and/or the mosaic image may be computed, for example, based on the detected lumen region. For each new frame (e.g., individual presented and/or added to the mosaic image), the 3D location of the central pixel and/or the direction of the 3D location of the central pixel relative to the detected 3D location of the lumen is computed. The 3D location of the lumen may be estimated from the 3D locations of the pixels in its close environment. The quarter covered by the current frame may be computed.

The estimated colon quarter depicted by the currently presented frame and/or mosaic image may be indicated to the user. An indication may be outputted when all four quarters have been covered indicating that the camera may be moved to a new location, and/or when one or more quarters have not been covered and the camera is moved another indication may be generated indicating lack of adequate imaging of the local colon region. Using the indication, the physician performing the colonoscopy procedure may determine whether the four quarters of the current local colon region are sufficiently covered with consecutive frames. A quarter that was sufficiently covered with a frame may be indicated for the user (e.g., for at least 5 seconds) so the user is able to see on the screen the combination of 4 indicated quarters together as a sign that the inner surface of the colon is sufficiently covered during the scanning of colon. A covered quarter may be indicated, for example, by its number appearing and/or blinking on the screen.

Figure 11:
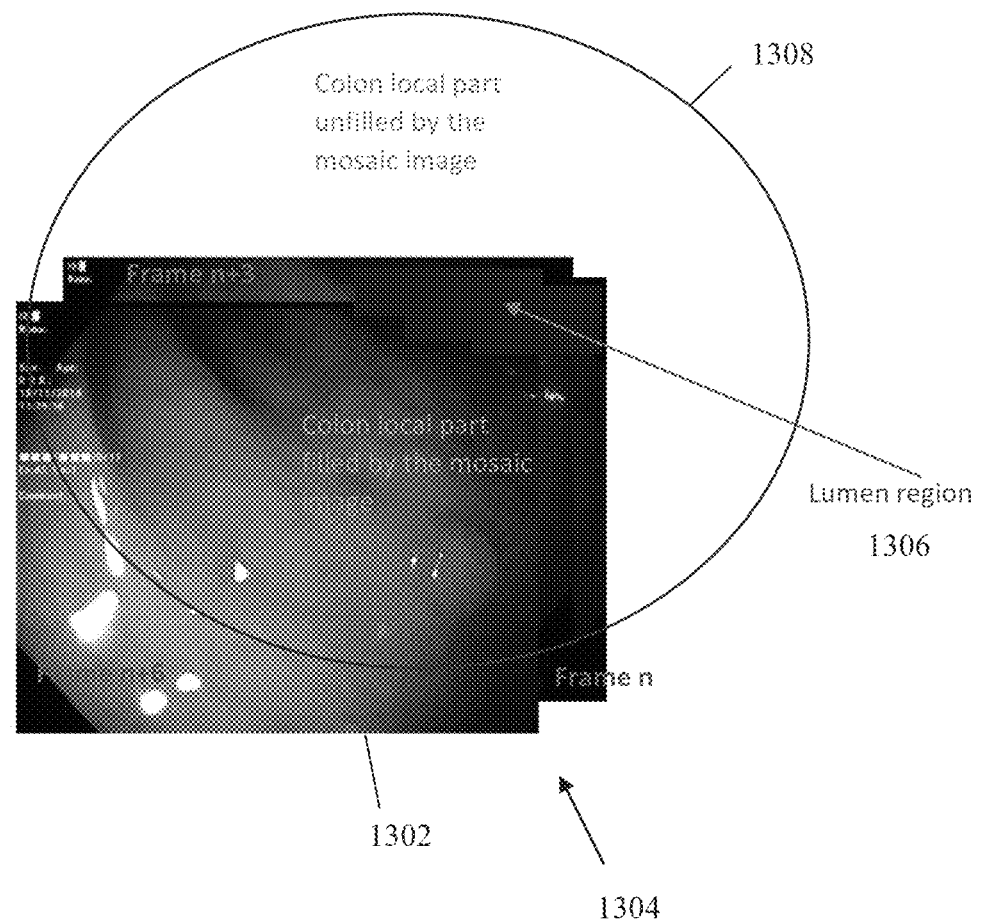
FIG. 11 is a schematic of a mosaic and/or panoramic image of the colon which is being built, for each pixel in the combined 2D images for which the 3D location in the single 3D coordinate system is computed, in accordance with some embodiments of the present invention.

Optionally, while the endoscope is being advance and/or retracted (e.g., on its way out from the colon, such as by being pulled out, from the cecum until the endoscope is completely removed out of the colon), the sequences of covered quarters is dynamically aggregated and/or tagged with the respective 3D location. The calculated trajectory of the endoscope (e.g., the endoscope is being advanced and/or retracted) may be scanned with a window of predefined length (e.g., about 2-3 cm) and/or with a predefined stride length (e.g., about 0.5-1 cm). If in numbers of consecutive scanned windows (denoted Ncs, having a value of, for example, 3) a certain quarter is not covered at all, then it is registered as a missed quarter. The percentage the colon that was covered by the endoscope camera while being advanced and/or pulled out may be calculated using the mathematical relationship:

$$\left(1 - \frac{Tms}{\frac{Nsw}{Ncs} * 4}\right) * 100$$

where Tms denotes the total number of missed quarters and Nsw denotes the total number of scanned windows. For example, when the total number of missed quarters (Tms) is 8, the total number of scanned windows (Nsw) is 100, and the number of consecutive scanned windows (Ncs) is 3, the percentage of colon that was covered according to the mathematical relationship is 76%. The computation of the percentage the colon that was covered by the endoscope camera may be performed, for example, dynamically in real time based on an aggregation of the images captured during the procedure, and/or off-line after the procedure has been completed using the set of images captured during the procedure. Reference is now made to FIG. 11, which is a schematic of a mosaic and/or panoramic image of the colon 1302 which is being built, for each pixel in the combined 2D images for which the 3D location in the single 3D coordinate system is computed, in accordance with some embodiments of the present invention. As shown, three 2D frames 1304 with step of 3 frames between each consecutive frame are used to create panoramic image 1302. A lumen region 1306 is depicted as a dark area in the center of the colon tube. Panoramic image 1302 covers only part of the local colon local region. Region 1308 remains unfiled by the mosaic image since now images have been captured of it.

Figure 12:
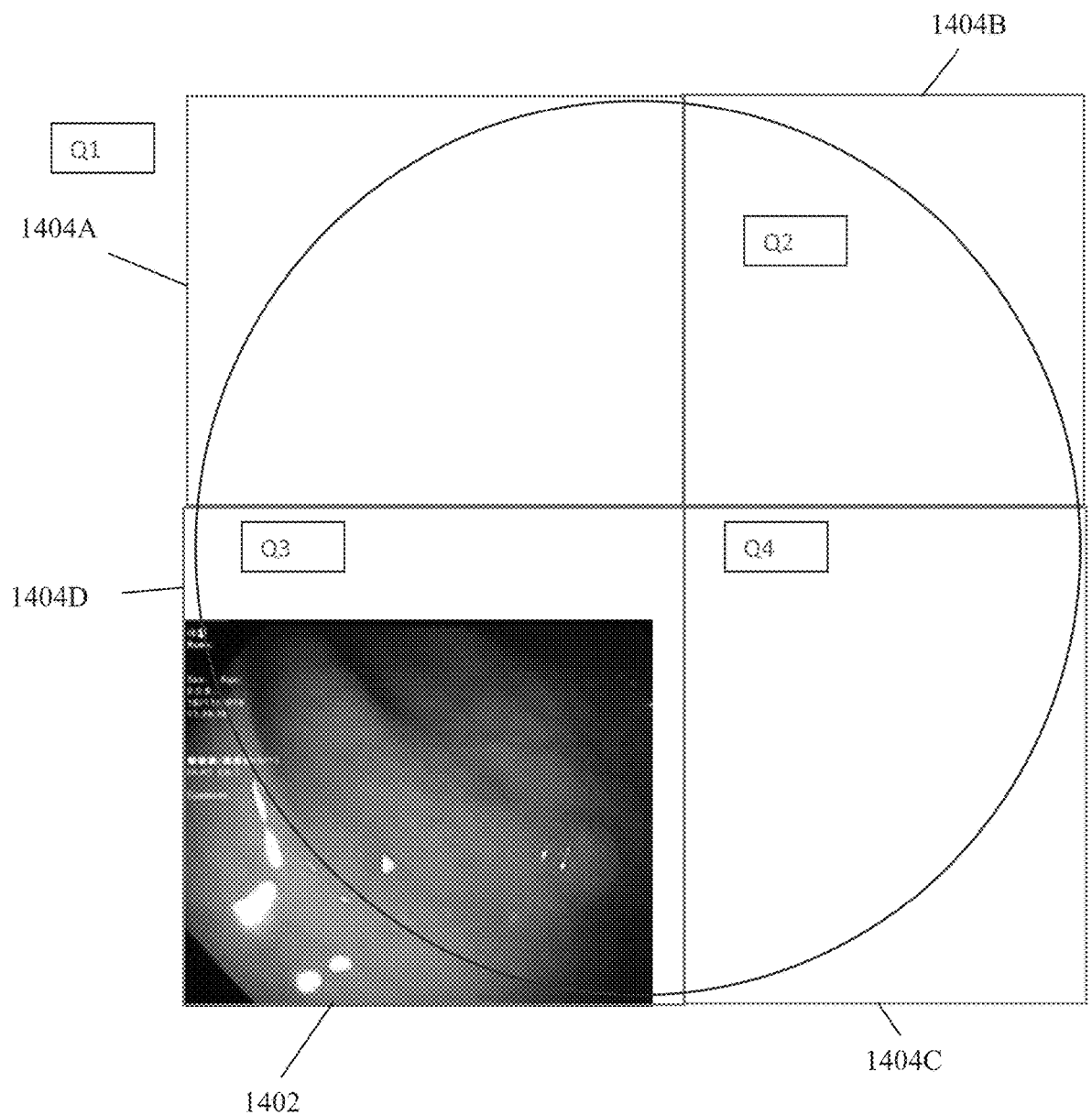
FIG. 12 is a schematic depicting an individual image, presented within the respective quarter of the inner surface of the colon depicted therein, in accordance with some embodiments of the present invention.

Reference is now made to FIG. 12, which is a schematic depicting an individual image 1402, presented within the respective quarter of the inner surface of the colon depicted therein, in accordance with some embodiments of the present invention. Portion 1404A denotes quarter 1, portion 1404B denotes quarter 2, portion 1404C denotes quarter 3, and portion 1404D denotes quarter 4.

Figure 13:
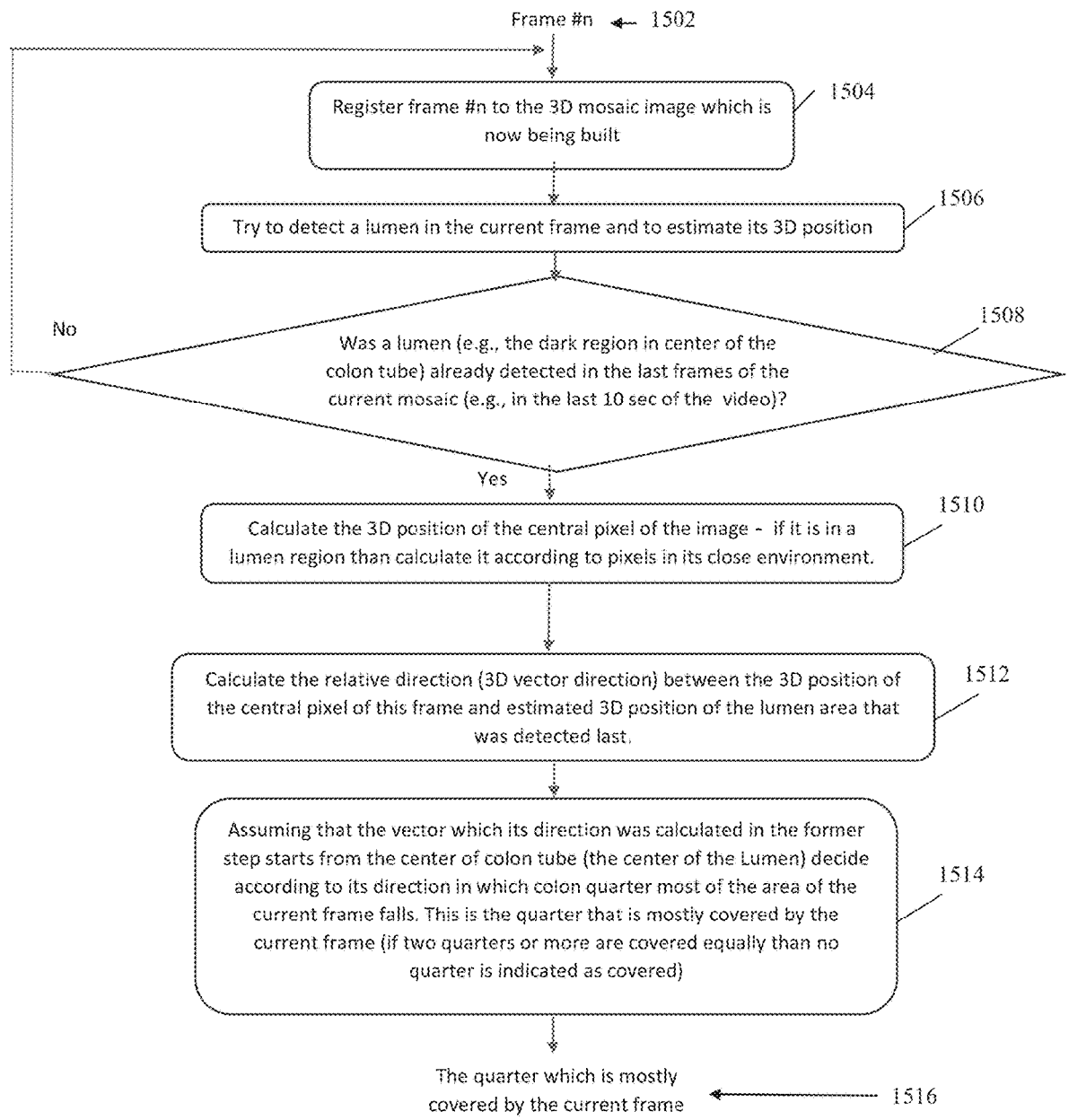
FIG. 13 is a flowchart of a method for calculating the quarter which is depicted by a frame, in accordance with some embodiments of the present invention.

Reference is now made to FIG. 13, which is a flowchart of a method for calculating the quarter which is depicted by a frame, in accordance with some embodiments of the present invention, it is noted that the selected quarter denotes the quarter mostly covered by the frame, since the frame may overlap between two or more quarters.

At 1502, the current frame (denoted #n) is provided.

At 1504, frame #n is registered to the 3D mosaic image which is now being built.

At 1506, a lumen may be detected in the current frame. The 3D position of the lumen may be estimated.

At 1508, when no lumen (e.g., the dark region in center of the colon tube) has already been detected in the last frames of the current mosaic (e.g., in the last 10 sec of the video), R02-R08 are iterated.

At 1510, when a lumen has been detected, the 3D position of the central pixel of the image—are calculated. When the central pixels are determined to be in a lumen region then the 3D position is calculated according to pixels in the close environment.

At 1512, the relative direction (e.g., 3D vector direction) between the 3D position of the central pixel of the current frame and estimated 3D position of the lumen area that was detected last is calculated.

At 1514, based on the assumption that the vector for which the direction was calculated in 1512 starts from the center of colon tube (i.e., the center of the Lumen), the colon quarter covering most of the area of the current frame is determined according to the direction of the vector. The selected quarter is the quarter that is mostly covered by the current frame (e.g., if two quarters or more are covered equally than no quarter is indicated as covered)

At 1516, the quarter depicted in the current frame is provided. Instructions for presenting an indication of the determined quarter in the GUI may be generated, as described herein.

Referring now back to FIG. 1, at 114, the dimension of the detected polyp is computed. The dimension may be a 2D and/or 3D dimension, for example, volume of the polyp, radius of a sphere representing the polyp, surface area of the polyp (e.g., flat polyp), and/or radius of 2D circle representing the polyp. The dimension may be computed by performing a best fit of a 3D sphere and/or 2D circle to the pixels of the 3D image (created from the 2D image as described herein, optionally by the 3D CNN) denoting the polyp. The dimension is obtained from the best fitted 3D sphere and/or 2D circle, for example, the radius of the best fitted 3D sphere and/or radius of the best fitted 2D circle.

The dimension(s) of the poly is computed based on ROI delineating the polyp computed and/or the 3D coordinates of the pixels of the 3D image (i.e., the 3D reconstruction of the 2D image) outputted by the 3D reconstruction neural network as described with reference to 108 and/or 110. The ROI delineating the polyp may be manually set by the operator (e.g., using the GUI) and/or automatically outputted by the detection network described with reference to 104 when fed the 2D image(s).

The process described herein enables computation of the dimension of the 3D volume and/or 2D surface area of the polyp using (optionally only using) the 3D coordinates values (x,y,z) computed for pixels in the 2D image as described herein (e.g., outputted by the 3D CNN). In contrast, other processes that compute 3D and/or 2D dimensions using 2D images require knowing properties of the camera (e.g., the pose of the camera relative to the polyp) which may be difficult to obtain.

The size of the polyp may be computed based on a radius of a circle which best fits the polyp slice.

The volume of the polyp may be calculated automatically by tasking the computed 3D values of the 2D pixels inside the polyp delineating contour and/or bounding box, and finding the best fitting 3D sphere (or circle if the polyp is flat) to the exposed 3D surface created by interpolating between the 3D values of the pixels. The radius of the sphere (or the circle) is the polyp size.

It is noted that the 3D volume may be computed from the computed radius of sphere correlated with the polyp, as described herein.

The estimated dimension (e.g., 3D volume) of the polyp(s) may be computed, for example, by the following process: Computing a best fitting 3D surface for the 3D coordinates of the pixels of the region of the at least one 2D image. Computing multiple normal vectors in proximity to a 3D location that correlates to a centroid of the region depicting the polyp (i.e., ROI). Determining the side of the 3D surface that is concave according to the relative directions of the normal vectors. Computing a plane that includes a normal vector of the multiple normal vectors that correlates to the 3D location that correlates to the centroid. Computing a vector at the 3D location that correlates to the centroid that is tangent to the best fitting 3D surface. Computing a first curvature as a radius of a tangent parabola of a contour that intersects between the best fitting 3D surface and the computed plane. Computing a second curvature as a radius of a tangent parabola of a contour that intersects between the best fitting 3D surface and an orthogonal plane that is orthogonal to the computed plane, where the orthogonal plane includes the normal vector. And computing a 3D radius of a 3D volume of the polyp as an average of the first curvature and second curvature.

Figure 14:
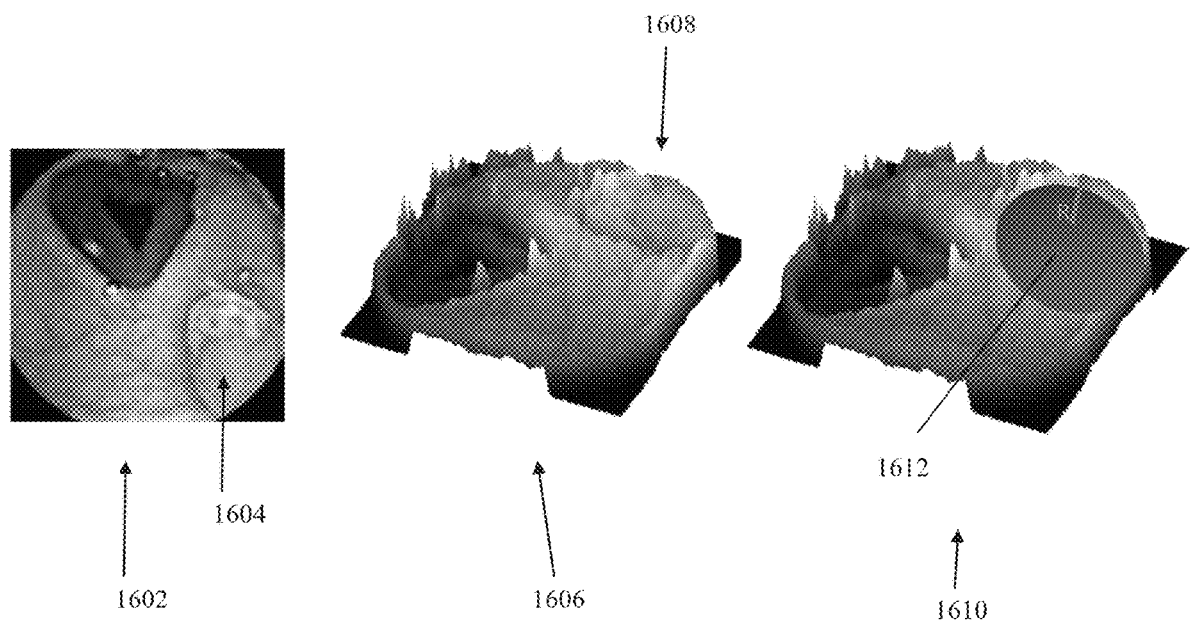
FIG. 14 is a schematic depicting the process for calculating a volume of a polyp from a 3D reconstructions surface computed from a 2D image, in accordance with some embodiments of the present invention.

Reference is now made to FIG. 14, which includes schematics depicting the process for calculating a volume of a polyp from a 3D reconstructions surface computed fro, a 2D image. In accordance with some embodiments of the present invention. Schematic 1602 denotes a 2D colonoscopy frame with a detected polyp 1604, obtained from the web address sites(dot)google(dot)com(slash)site(slash)suryaiit(slash)research(slash)endoscopy(slash)sfs. Schematic 1606 denotes the 3D reconstructed surface of frame 1602. Polyp 1608 is the 3D reconstructions of polyp 1604 of 2D image 1602. Image 1610 depicts the process of calculation of the volume of the polyp by finding the best fitting (tangent) 3D sphere 1612 to concave side of the surface interpolated from the 3D values of the pixels inside the polyp region, as described herein. The volume is the radius (R) of 3D Sphere 1612.

Figure 15:
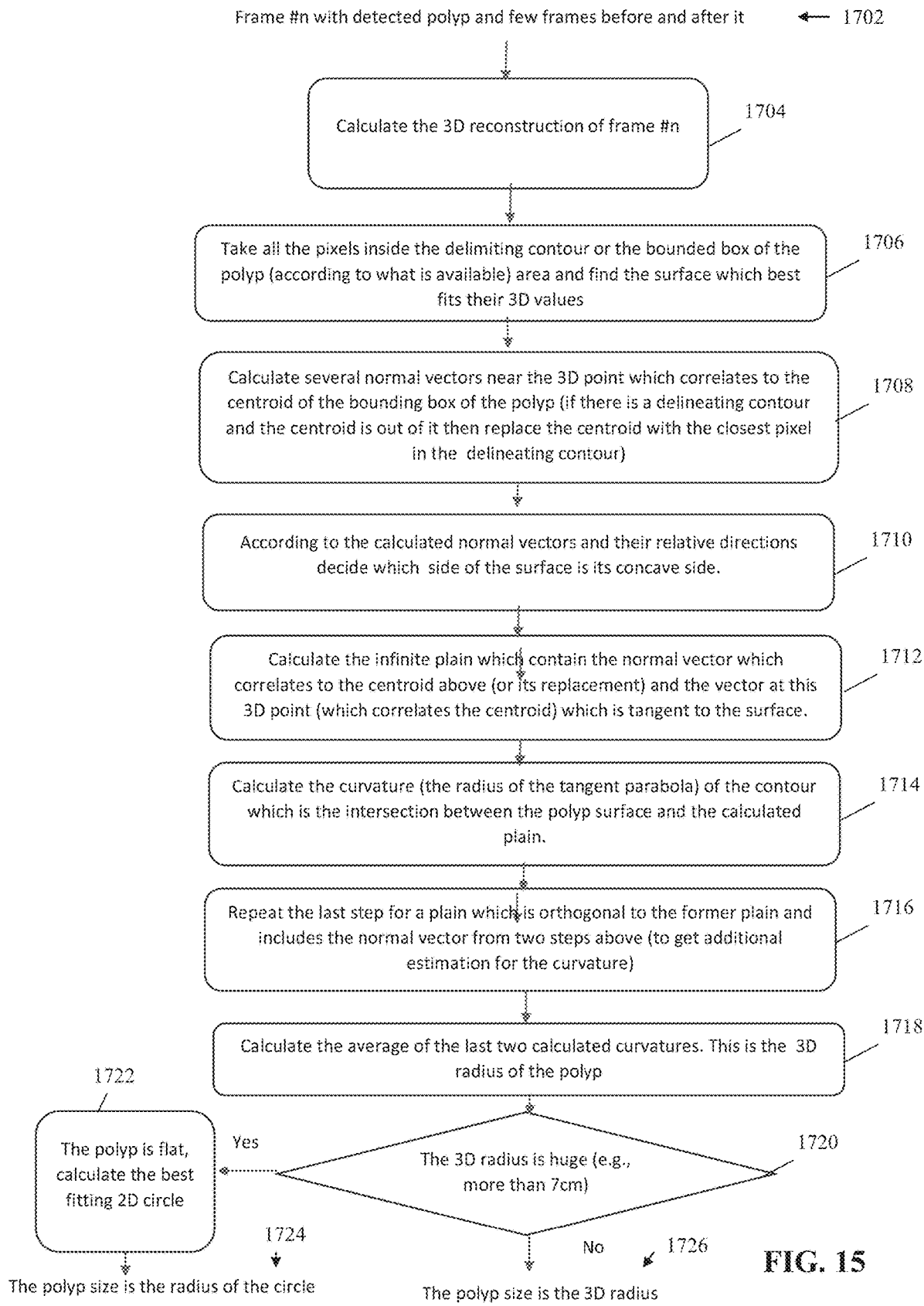
FIG. 15 is a flowchart of an exemplary process for computing volume of a polyp from a 2D image, in accordance with some embodiments of the present invention.

Reference is now made to FIG. 15, which is a flowchart of an exemplary process for computing volume of a polyp from a 2D image, in accordance with some embodiments of the present invention.

At 1702, the 2D frame denoted #n with detected polyp is received. Multiple frames before and after the current frame are received.

At 1704, the 3D reconstruction of frame #n is computed, as described herein.

At 1706, the pixels inside the delimiting contour and/or the bounded box of the polyp (according to what is available) area are identified, and the surface which best fits their 3D values is computed.

At 1708, multiple normal vectors near the 3D point which correlates to the centroid of the bounding box of the polyp are computed (when there is a delineating contour and the centroid is out of the delineating contour then the centroid is replaced with the closest pixel in the delineating contour).

At 1710, the concave side of the surface is identified according to the calculated normal vectors and their relative directions.

At 1712, the infinite plain which contain the normal vector which correlates to the centroid above (or its replacement) and the vector at this 3D point (which correlates the centroid) which is tangent to the surface, are calculated.

At 1714, the curvature (the radius of the tangent parabola) of the contour which is the intersection between the polyp surface and the calculated plain is computed, for example, based on the approach described with reference to Har'el, Zvi. "*Curvature of curves and surfaces—a parabolic approach.*" *Department of Mathematics, Technion—Israel Institute of Technology* (1995).

At 1716, the last step for a plain which is orthogonal to the former plain and includes the normal vector from 1712 and 1714 is repeated (to get additional estimation for the curvature).

At 1718, the average of the last two calculated curvatures is computed, providing the 3D radius of the polyp.

At 1720, when the 3D radius is greater than a predefined threshold (e.g., 7 millimeters, 7 centimeters or other value), at 1722, the polyp size is denoted to be flat. The best fitting 2D circle is computed. The size of the polyp is defined according to the size of the 2D circle. At 1726, when the 3D radius is less than the predefine threshold, the polyp size is defined according to the 3D radius.

Reference is now made back to FIG. 1. At 116, instructions for updating a presentation of a GUI are generated. The image may be augmented. The instructions may be, for example, for injecting GUI elements into the image, for presenting an overlay over the image, and/or for presenting the image within one part of the GUI and presenting other graphical elements within another part of the GUI, for example, the covered quadrants and/or the colon map, as described herein.

The instructions are generated based on the outputs of one or more features described with reference to 104-114:

Instructions are generated for augmenting the image with the location of the polyp detected as described with reference to 104, for example, marking the ROI (e.g., boundary box) delineating the detected polyp, and/or color coding the polyp and/or boundary box, and/or an arrow pointing to the polyp.

Instructions are generated based on the indication of the vector that points from the current image towards the ROI depicting the polyp located externally to the current image, as described with reference to feature 106. The instructions are for creating an augmented endoscopic image by augmenting the respective endoscopic image with an indication of the vector.

The vector may be presented as an arrow. The arrow points in the direction that the camera should be moved to in order to re-capture the polyp within the image. The arrow and the images may be presented in 2D.

Optionally, when the polyp is re-captured in the image (e.g., after moving the camera in the direction of the arrow), the instructions are generated for augmenting the image with the ROI depicting the poly. The ROI may be re-marked on the image without necessarily executing feature 104, i.e., based on the tracking alone.

Optionally, instructions are generated for presenting a colon map within the colon, based on the output of features described with reference to 106 and/or 110. The 2D and/or 3D location of the polyp (e.g., the ROI depicting the polyp) is obtained, for example, outputted by the detection neural network and/or the 3D reconstruction neural network, and/or manually marked by the operator (e.g., using the GUI, such as by pressing a "polyp" icon). The location of the polyp is marked on a schematic representation of a colon of the patient with an indication, for example, an X, and/or a circle, optionally color coded according to whether the polyp was identified during insertion of the colonoscope and/or removal of the colonoscope. The colon map is dynamically update with new detected polyps.

Optionally, instructions are generated for marking the polyps presented on the colon map with an indication of treatment (e.g., surgical removal, ablation). For example, polyps presented as ovals within the colon map that were removed are marked with an X. Ovals within the map that have not been removed are not marked with the X. The polyps are marked as treated based on an indication of removal of the polyp, for example, manually provided by the user (e.g., pressing a "polyp removed" icon on the GUI) and/or automatically detected by code (e.g., based on a detection of movement of surgical tools in the colonoscope).

Optionally, instructions are generated for plotting tracked 3D locations of the endoscope on the colon map presented within the GUI, for example, as trajectories and/or curves and/or dotted lines. The trajectories and/or curves and/or dotted lines are dynamically updated as the endoscope is moved (e.g. forward and/or reverse) in the colon. Optionally, forward direction tracked 3D locations are marked on the colon map with a marking denoting a forward direction (e.g., from rectum to cecum) of the endoscopic camera entering deeper into the colon, for example, arrows in the forward direction and/or using a color coding. Reverse direction tracked 3D locations presented on the colon map are marked with another marking denoting a reverse direction (e.g., from cecum to rectum) of the endoscopic camera being removed from the colon, for example, arrows in the reverse direction and/or a different color.

Optionally, instructions for presenting the computed dimension of the detected polyp are generated. For example, the computed dimension is presented as a numerical value optionally with units in proximity to the ROI marked on the image, for example, the value of the computed volume in cubic millimeters. In another example, the computed dimension is presented as a numerical value with unit in proximity to the indication of the polyp on the colon map.

Optionally, instructions for presenting an alert within the GUI indicating of a suggestion to remove the polyp are generated when the dimension is above a threshold. For example, when the radius of a sphere defining the 3D volume of the polyp is above 2 millimeters. The alert may be generated, for example, as a coloring of the polyp and/or border of the ROI delineating the polyp on the image using a unique color denoting a suggestion to remove (e.g., red for removal and green to leave in), and/or coloring of the polyp representation on the colon map, and/or audio message, and/or pop-up text message within the GUI.

Optionally, instructions for presenting an estimate of remaining portions of the inner surface area not yet depicted within any previously captured endoscopic images are generated. Alternatively or additionally, instructions for presenting an estimate of portions of the inner surface area already depicted are generated. For example, a GUI element in the shape of a circle divided into 4 quadrants (or other number of divisions, for example, as slices) is presented. Quadrants depicted in images are shown with one marking, for example, colored green. Quadrants not yet depicted are shown with a different marking, for example, colored red. The operator may view the marked (e.g., color coded circle), and orient the camera in the direction towards the not yet imaged quadrants. Once the GUI element depicts that all quadrants have been imaged, the operator may displace the colonoscope (e.g., forward or backwards).

The quadrants may depict regions that have mostly been imaged, for example, greater than 50%, or 70% or 80% of the surface of the quadrant is depicted in one or more images. Other divisions may be selected according to the imaging capabilities of the lens of the camera, for example, a greater number of divisions may be used for narrow angle lens.

Optionally, instructions for presenting an alert are generated when the current location of the camera is close to the anatomical landmark and/or polyp, according to predefined system definitions (which may be set, for example, from time to time by a setup menu). For example, the definitions may be set to generate an alert when the location of the camera is close to a location of the landmark, when the distance is before a predefined threshold. The distance between the camera and landmark and/or polyp may be calculated, for example, by L2 metric and/or a proximity which is small enough in order give an alert (e.g., about 3 centimeters). The threshold distance value may take into consideration the aggregated calculation error of building the trajectory, and/or the fact that the colon itself is not completely stable in the stomach, namely not stable in the coordinate system in which the trajectory is being built.

Optionally, the amount of time that the endoscope spends in each defined part of the colon may be calculated and presented. Each part may be defined, for example, according to the transition points between anatomical landmarks that divide the colon into parts, for example, the Ascending colon and the Transverse colon (e.g., between the Transverse colon and the Ascending colon). The anatomical landmarks may be detected manually by the user (e.g., user marks the landmark using the GUI) and/or automatically by code (e.g., based on an analysis of the images). 3D locations of the endoscopic camera relative to the anatomical landmark(s) are tracked. An amount of time spent by the endoscopic camera in each of the parts of the colon is computed. Instructions for presenting the amount of time spent by the endoscopic camera in each of the parts of the colon in the GUI are generated. The time may be presented, for example, as a marking on the respective part of the colon map corresponding to the part of the colon of the patient.

At 118, the generated instructions are implemented. The GUI is updated according to the instructions.

Figure 16:
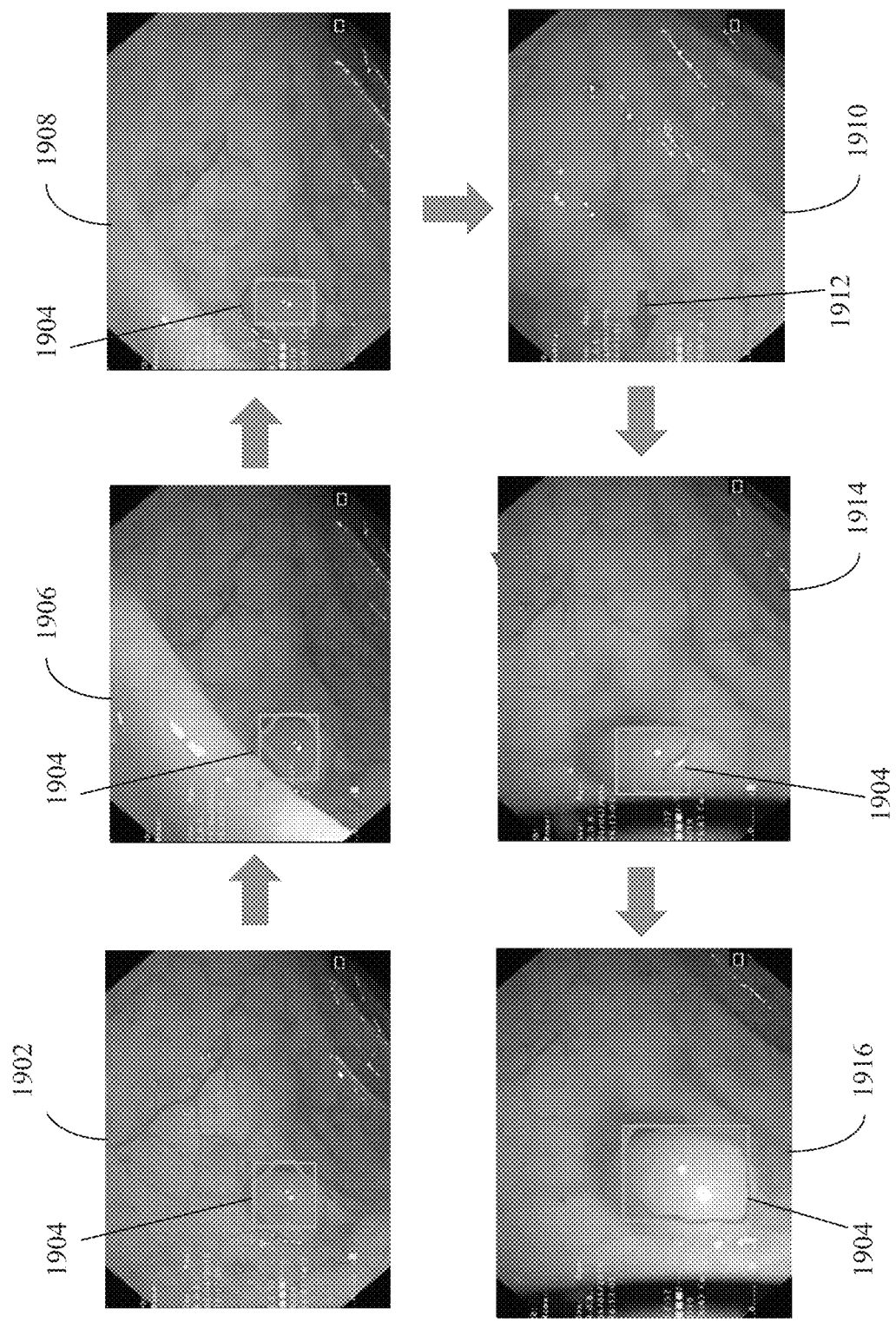
FIG. 16 is a schematic depicting a sequence of augmented images for tracking an ROI of a polyp presented within the GUI according to the generated instructions, in accordance with some embodiments of the present invention.

Reference is now made to FIG. 16, which is a schematic depicting a sequence of augmented images for tracking an ROI of a polyp presented within the GUI according to the generated instructions, in accordance with some embodiments of the present invention. The sequence depicts 2D tracking of the polyp, and generation of an arrow in the direction of the polyp when the polyp is located externally to the image, as described herein. Image 1902 is a first image, augmented with an ROI 1904 depicting the automatically detected polyp. In a second image of the sequence 1906, ROI 1904 has moved towards the left of the image due to a re-orientation of the camera. In a third image of the sequence 1908, ROI 1904 has moved even further to the left of the image. In a fourth image of the sequence 1910, the ROI is located externally to the image and therefore is not depicted in image 1910. An arrow 1912 is presented pointing in the direction of the externally located ROI. In a fifth image of the sequence 1914, ROI 1904 has re-appeared after the operator has re-oriented the camera in the direction pointed to by arrow 1912 of image 1910. In a sixth image of the sequence 1916, ROI 1904 has moved more to the right due to a movement of the camera by the operator.

Figure 17:
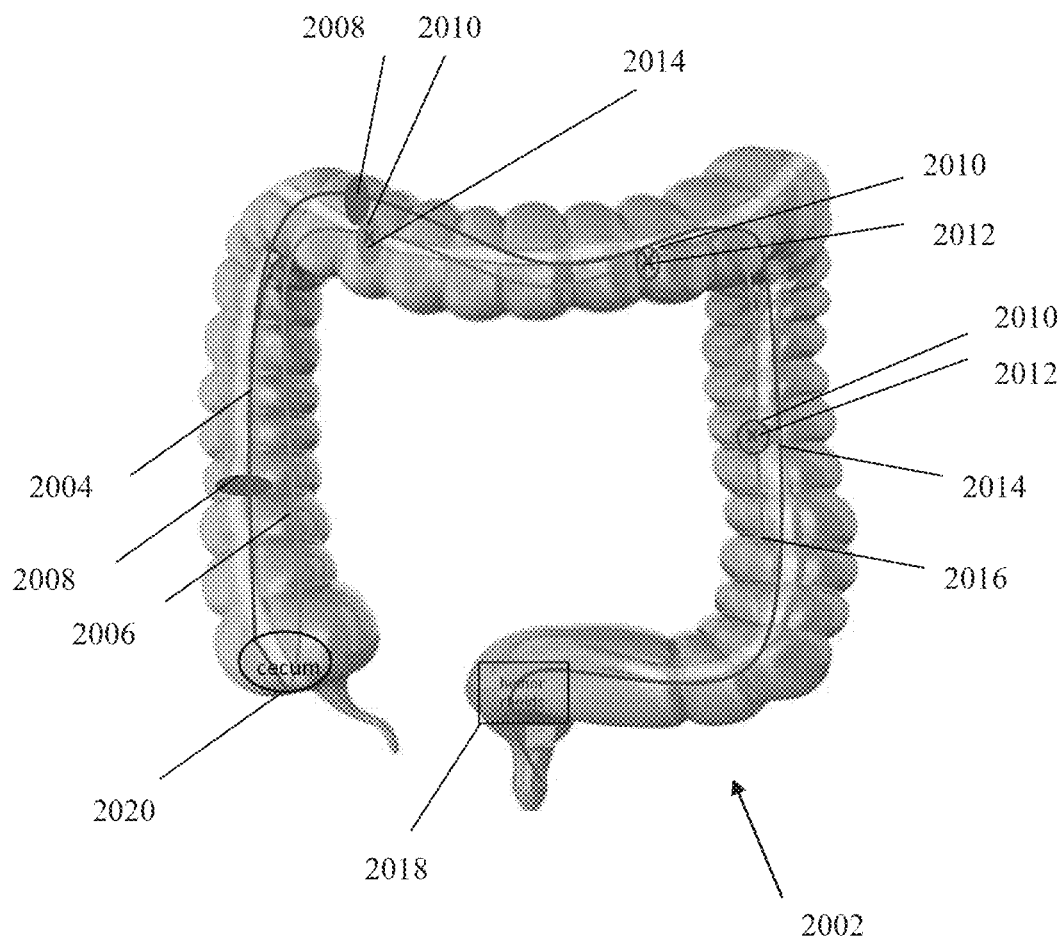
FIG. 17 is a schematic of a colon map that presents trajectories of movement of the endoscope, locations of detected polyps, removed polyps, and anatomical landmarks, presented within the GUI, in accordance with some embodiments of the present invention.

Reference is now made to FIG. 17, which is a schematic of a colon map 2002 that presents trajectories of movement of the endoscope, locations of detected polyps, removed polyps, and anatomical landmarks, presented within the GUI, in accordance with some embodiments of the present invention. Colon map 2002 may be presented, for example, as an overlap presented on a corner of the images, or in a designated window of a GUI having another designated window for presenting the images. Trajectory 2004 depicts the tracked 3D movement of the endoscope during forward movement into the colon, for example, color coded. Trajectory 2006 depicts the tracked 3D movement of the endoscope during reverse movement out of the colon, for example, color coded with a different color. Ovals 2008 denote polyps automatically detected during the forward movement of the colonoscope, for example, colored with the same color used for forward trajectory 2004. Ovals 2010 denote polyps automatically detected during the reverse movement of the colonoscope, for example, colored with the same color used for reverse trajectory 2006. Circle 2012 denotes a polyp that was manually found by the user, and/or an automatically detected polyp that is manually marked by the user. An X marking 2014 denotes a polyp that was removed by the operator. Arrow head 2016 notes the current 3D location of the distal end (e.g., tip) of the endoscope, optionally the camera. Box 2018 denotes a manually designated landmark manually entered by the user (e.g., via the GUI), for example, hemorrhoids. Circle 2020 denotes an automatically identified landmark, for example, detected by an analysis of the 3D reconstructed images. Colon map 2002 is dynamically updated as the colonoscope is moved, as polyps are detected, and/or as polyps are removed.

Figure 18:
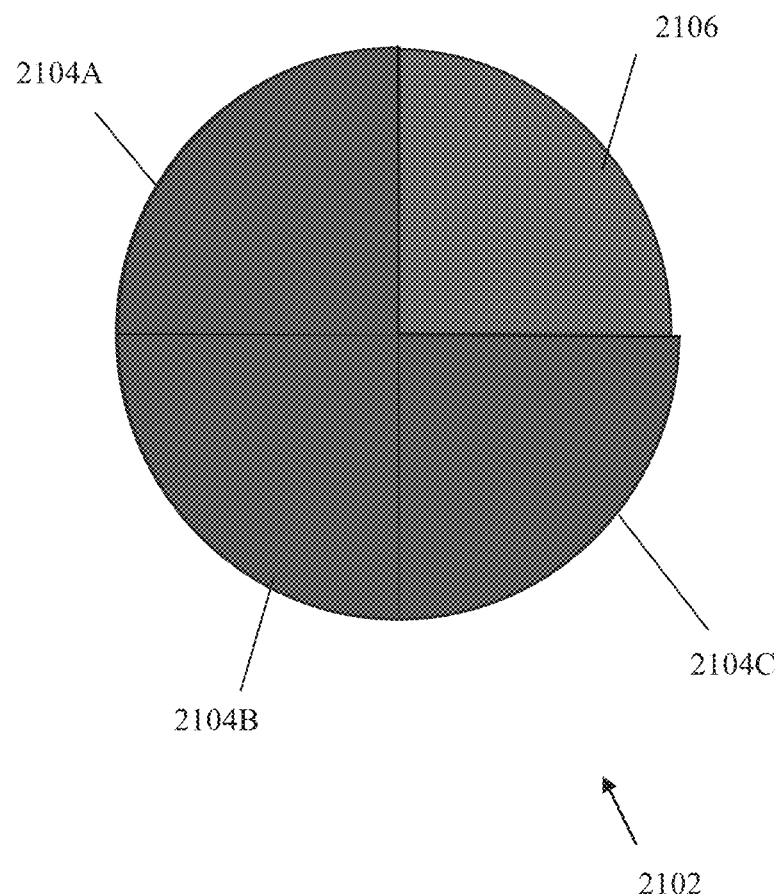
FIG. 18 is a schematic depicting quadrants of the inner surface of the colon depicted in one or more images and/or quadrants of the inner surface of the colon not yet depicted in images, in accordance with some embodiments of the present invention.

Reference is now made to FIG. 18, which is a schematic 2102 depicting quadrants of the inner surface of the colon depicted in one or more images 2104A-C and/or quadrants of the inner surface of the colon not yet depicted in images 2106, in accordance with some embodiments of the present invention. Schematic 2102 is created for each new location of the camera, as the camera is displaced forward and/or backwards. Alternatively or additionally, schematic 2102 is computed for a recent defined time window (e.g., 5 seconds, or 10 seconds, or other values). The time window may be short enough to exclude movement of the camera forward and/or backwards, but long enough to enable full imaging of the circumference of the inner wall for the colon. Quadrants are updated as new images are acquired at the same location by re-orienting the camera. Quadrants 2104A-C and 2106 may be color coded. Schematic 2102 is dynamically updated as the operator moves the camera to image the remaining portions of the inner surface of the colon.

At 120, one or more features described with reference to 100-118 are iterated. The iterations may dynamically update the GUI, for example, for dynamically tracking the polyps, dynamically generating arrows pointing to ROIs delineating polyps located externally to the current image, updating the colon map with new 2D and/or 3D locations of polyps, updating the camera trajectory of the colon map with movement of the camera, updating the GUI to depict coverage of the inner surface of the colon (e.g., quadrads), and/or updating computed 2D and/or 3D dimensions of the detected polyps.

The updated GUI may be used by the operator, for example, for maneuvering the camera to capture images of polyps, for determining which polyps to remove, for maneuvering the camera to ensure full coverage of the internal surface of the colon, and/or for tracking the location of the camera and/or detected polyps within the colon.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant endoscopes will be developed and the scope of the term endoscope is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of generating instructions for presenting a GUI for dynamically tracking 3D movement of an endoscopic camera capturing a plurality of 2D endoscopic images within a colon of a patient, comprising:
   iterating for respective endoscopic images of a plurality of endoscopic images:
      feeding the respective 2D endoscopic image into a 3D reconstruction neural network;
      outputting by the 3D reconstruction neural network, a 3D reconstruction of the respective 2D endoscopic image, wherein pixels of the 2D endoscopic image are assigned 3D coordinates;
      computing according to the 3D reconstruction, a current 3D location within the colon of the endoscopic camera;
      generating instructions for presenting the current 3D location of the endoscopic camera on a colon map within the GUI;
   analyzing the respective 3D reconstruction to estimate a portion of an inner surface of the colon depicted within the respective endoscopic image, tracking cumulative portions of the inner surface of the colon depicted within successive endoscopic images during a spiral scanning motion of the endoscopic camera during a colonoscopy procedure, and generating instructions for presenting within the GUI, at least one of: an estimate of remaining portions of the inner surface not yet depicted within any previously captured endoscopic images, and an estimate of total coverage of the of the inner surface area, wherein the analyzing, the tracking, and the generating are iterated during the spiral scanning motion.

2. The method of claim 1, further comprising:
   tracking 3D locations of the endoscopic camera; and
   plotting the tracked 3D locations of the endoscopic camera within the colon map GUI.

3. The method of claim 1, wherein forward direction tracked 3D locations of the endoscopic camera are marked on the colon map presented in the GUI with a marking denoting a forward direction of the endoscopic camera entering deeper into the colon, and reverse direction tracked 3D locations of the endoscopic camera presented on the colon map are marked with another marking denoting a reverse direction of the endoscopic camera being removed from the colon.

4. The method of claim 1, further comprising
   feeding the respective endoscopic image into a detection neural network;
   outputting, by the detection neural network, an indication of a region of the endoscopic image depicting at least one polyp; and
   computing an estimated 3D location of the at least one polyp within the region of the endoscopic image according to the 3D reconstruction, and generating instructions for presenting the 3D location of the at least one polyp on a colon map within the GUI.

5. The method of claim 4, further comprising:
   receiving an indication of surgical removal of the at least one polyp from the colon; and
   marking the 3D location of the at least one polyp on the colon map with an indication of removal of the at least one polyp.

6. The method of claim 4, further comprising:
   tracking a 3D location of an endoscopic camera capturing the plurality of endoscopic images;
   computing an estimating distance from a current 3D location of the endoscopic camera to a 3D location of at least one polyp previously identified using earlier obtained endoscopic images; and generating instructions for presenting an indication within the GUI when the estimated distance is below a threshold.

7. The method of claim 1, wherein each portion corresponds to a time window having an interval corresponding to an amount of time for covering the respective portion during the spiral scanning motion, wherein an indication of adequate coverage is generated when at least one image depicting mostly the respective portion is captured during the time window and/or another indication of inadequate coverage is generated when no images depicting mostly the respective portion are captured during the time window.

8. The method of claim 7, wherein an indication of a total amount of the inner surface depicted in images relative to an amount of non-depicted inner surface is computed by aggregating the portions covered during the spiral scanning motion relative to the portions not covered during the spiral scanning motion.

9. The method of claim 1, wherein the 3D reconstruction neural network is trained by a training dataset of pairs of 2D endoscopic images defining input images corresponding 3D coordinate values computed for pixels of the 2D endoscopic images computed by a 3D reconstruction process defining ground truth.

10. The method of claim 1, further comprising:

receiving an indication of at least one anatomical landmark of the colon, wherein the at least one anatomical landmark divides the colon into a plurality of parts;

tracking 3D locations of the endoscopic camera relative to the at least one anatomical landmark;

computing an amount of time spent by the endoscopic camera in each of the plurality of parts of the colon; and generating instructions for presenting the amount of time spent by the endoscopic camera in each of the plurality of parts of the colon in the GUI.

* * * * *